United States Patent
Nelson et al.

(10) Patent No.: US 11,882,884 B2
(45) Date of Patent: *Jan. 30, 2024

(54) APPARATUS AND METHOD FOR ASSEMBLING A HEATER ASSEMBLY FOR A NICOTINE POD ASSEMBLY

(71) Applicant: Altria Client Services LLC, Richmond, VA (US)

(72) Inventors: Gregory L. Nelson, Chester, VA (US); Bipin Patil, Richmond, VA (US); Craig Gunn, Richmond, VA (US); Rangaraj S. Sundar, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 869 days.

This patent is subject to a terminal disclaimer.

(21) Appl. No.: 16/856,476

(22) Filed: Apr. 23, 2020

(65) Prior Publication Data
US 2021/0329976 A1    Oct. 28, 2021

(51) Int. Cl.
| | |
|---|---|
| *A24F 40/70* | (2020.01) |
| *B25B 11/02* | (2006.01) |
| *B23P 19/00* | (2006.01) |
| *A24F 40/46* | (2020.01) |
| *A24F 40/44* | (2020.01) |
| *A24F 40/42* | (2020.01) |
| *A61M 11/04* | (2006.01) |

(52) U.S. Cl.
CPC .............. *A24F 40/70* (2020.01); *A24F 40/42* (2020.01); *A24F 40/44* (2020.01); *A24F 40/46* (2020.01); *B23P 19/001* (2013.01); *B25B 11/02* (2013.01); *A61M 2207/00* (2013.01); *A61M 2207/10* (2013.01)

(58) Field of Classification Search
CPC ........ B25B 11/02; B23P 19/001; B23P 19/04; B23P 19/10; A24F 40/70; A61M 2207/00–10; H05B 2203/017
See application file for complete search history.

(56) References Cited

U.S. PATENT DOCUMENTS

| | | | |
|---|---|---|---|
| 2014/0157583 A1* | 6/2014 | Ward ....................... H05B 3/00 |
| | | | 29/729 |
| 2014/0261408 A1 | 9/2014 | DePiano et al. | |

(Continued)

FOREIGN PATENT DOCUMENTS

| | | | |
|---|---|---|---|
| EP | 2779786 A1 | 9/2014 | |
| EP | 2928330 A1 | 10/2015 | |
| WO | WO-2016065605 A1 * | 5/2016 | ............ A24F 47/00 |

OTHER PUBLICATIONS

Translation of WO-2016065605-A1 (Year: 2016).*

(Continued)

*Primary Examiner* — Matthew P Travers
(74) *Attorney, Agent, or Firm* — Harness, Dickey & Pierce, P.L.C.

(57) ABSTRACT

An apparatus for assembling a heater assembly for a nicotine pod assembly includes a base, a wick feed, a slide, and a holder. The wick feed extends toward the base and defines a channel configured to receive a wick structured to draw a nicotine pre-vapor formulation via capillary action. The slide is configured to move along a plane on a top face of the base. The holder is disposed on the top face of the base.

19 Claims, 33 Drawing Sheets

(56) References Cited

U.S. PATENT DOCUMENTS

| | | | | |
|---|---|---|---|---|
| 2016/0192711 A1* | 7/2016 | Xiang | ............... | B21F 3/04 29/745 |
| 2017/0224021 A1* | 8/2017 | Xiang | ............... | H05B 3/42 |
| 2021/0195955 A1* | 7/2021 | Shibuya | ............ | A24F 40/46 |
| 2021/0329976 A1* | 10/2021 | Nelson | ............ | A24F 40/42 |

OTHER PUBLICATIONS

International Search Report and Written Opinion dated Aug. 4, 2021 in corresponding application PCT/EP2021/060752.
International Search Report and Written Opinion dated Jul. 23, 2021 in corresponding application PCT/US2021/025354.
International Preliminary Report on Patentability dated Apr. 14, 2022 issued in corresponding application No. PCT/EP2021/060752.
U.S. Office Action for U.S. Appl. No. 16/856,291 dated May 31, 2023.
U.S. Notice of Allowance for U.S. Appl. No. 16/856,291 dated Sep. 21, 2023.

* cited by examiner

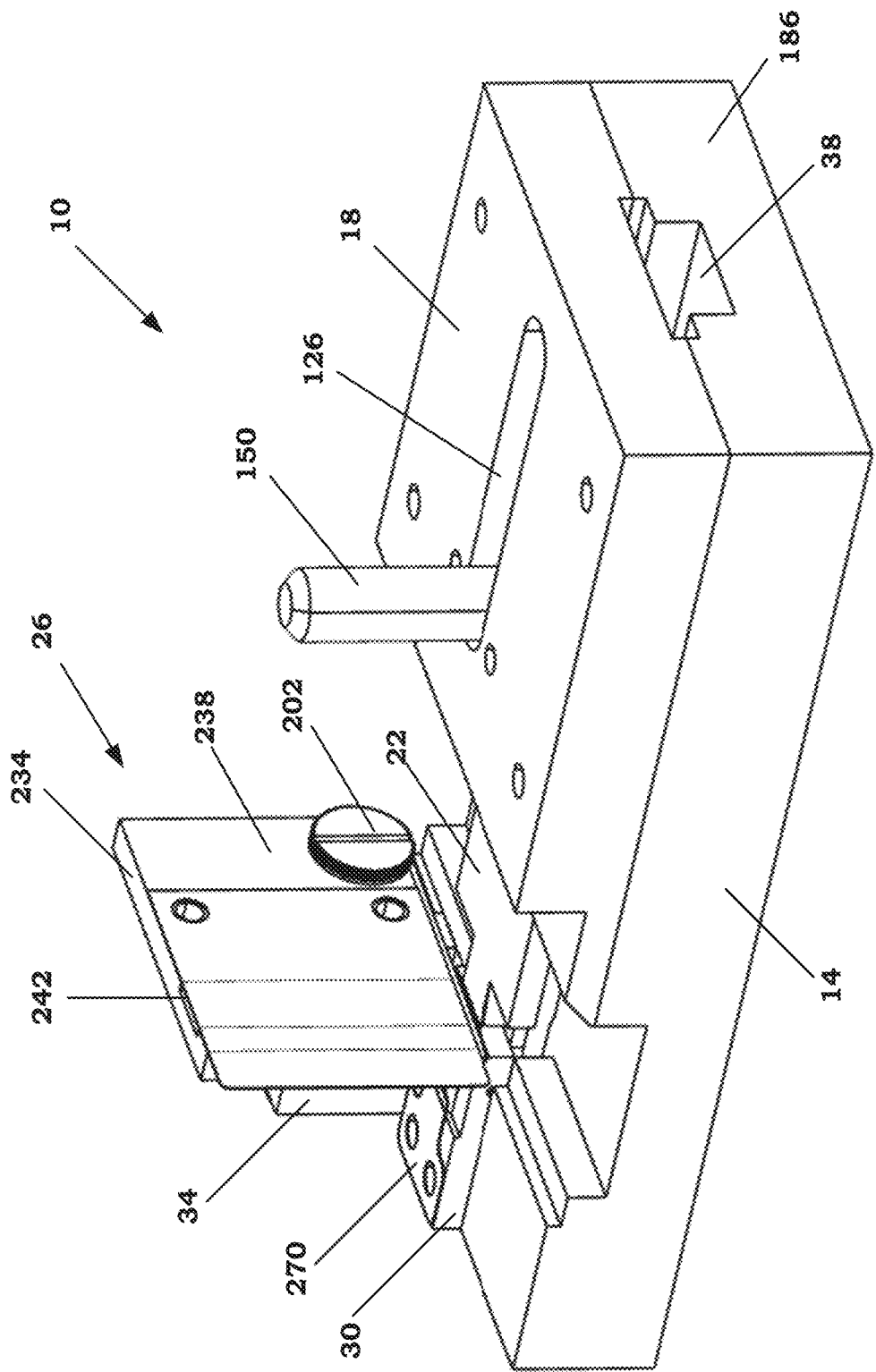

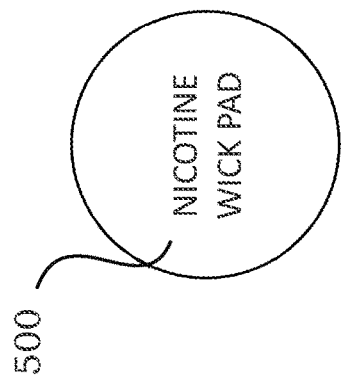
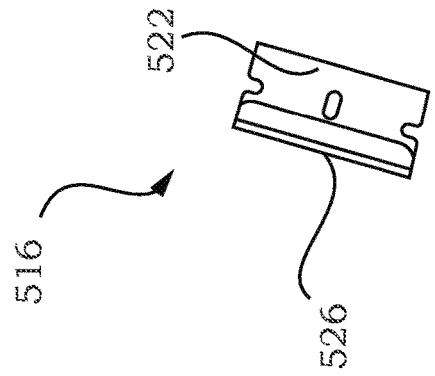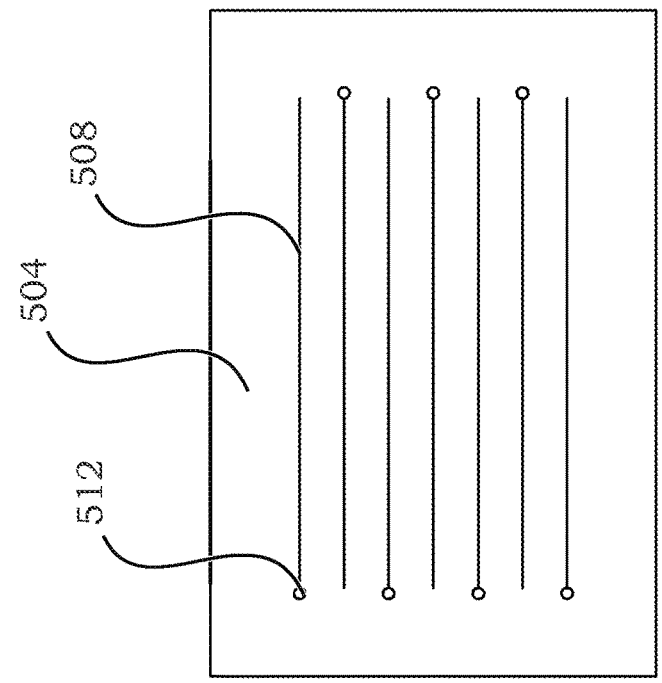

APPARATUS AND METHOD FOR ASSEMBLING A HEATER ASSEMBLY FOR A NICOTINE POD ASSEMBLY

BACKGROUND

Field

The present disclosure relates to an apparatus used in the preparation and assembly of a heater assembly for a nicotine pod assembly.

Description of Related Art

A nicotine electronic vaping or e-vaping device includes a heating element that vaporizes a nicotine pre-vapor formulation to produce a nicotine vapor.

A nicotine e-vaping device includes a power supply, such as a rechargeable battery, arranged in the device. The power supply is electrically connected to the heater. The power supply provides power to the heater such that the heater heats to a temperature sufficient to convert the nicotine pre-vapor formulation to a nicotine vapor. The nicotine vapor exits the nicotine e-vaping device through a mouthpiece including at least one outlet.

SUMMARY

This section provides a general summary of the disclosure, and is not a comprehensive disclosure of its full scope or all of its features.

At least one example embodiment relates to an apparatus for assembling a heater assembly for a nicotine pod assembly and includes a base, a wick feed, a slide, and a holder. The wick feed extends toward the base and defines a channel configured to receive a wick structured to draw a nicotine pre-vapor formulation via capillary action. The slide is configured to move along a plane on a top face of the base. The holder is disposed on the top face of the base.

The example apparatus may include a wick retainer extending parallel and adjacent to the wick feed for retaining the wick in the channel.

The example apparatus may include a cutter having a blade configured to slide along a top surface of the slide to cut the wick.

The wick feed in the example apparatus may be configured to rotate relative to the base.

The example apparatus may include a block fixed to the base. The wick feed may be rotatably attached to and supported by the block.

The holder of the example apparatus may be configured to receive a support of the heater assembly therein, the holder being configured to fix the support relative to the base for inserting the wick.

The channel in the wick feed of the example apparatus may be configured to guide the wick into alignment with a heater on the support.

The wick feed of the example apparatus may extend orthogonally to the base.

The holder of the example apparatus may include a locking finger configured to engage a support of the heater assembly and retain the support within the holder.

The holder of the example apparatus may be configured to secure a support of the heater assembly. The slide may include a front face that is orthogonal to the top face of the base. The slide may be configured to contact a finger of a heater on the support to move the finger to a vertical position so as to compress the wick.

The wick feed of the example apparatus may include a plate and a retainer. The plate may be disposed orthogonal to the base and may define the channel. The retainer may be disposed orthogonal to the base and adjacent to the plate. The retainer and the plate may define a slot for guiding the wick.

The example apparatus may include a block fixed to the base. The plate may be rotatably attached to and supported by the block.

The retainer of the example apparatus may be fixed to the plate such that the retainer and the plate are configured to rotate relative to the base and the block.

The holder of the example apparatus may be configured to secure a support of the heater assembly and to lock a position of the support relative to the base.

The holder of the example apparatus may include a locking finger configured to engage the support and retain the support within the holder.

The example apparatus may include a blade configured to slide along a top surface of the slide.

At least one example embodiment relates to a method of assembling a heater assembly for a nicotine pod assembly and includes securing, with a holder, a support of the heater assembly relative to a base; aligning, with a guide plate mounted to the base, a wick strip in a heater of the support, the wick strip structured to draw a nicotine pre-vapor formulation via capillary action; cutting, with a blade configured to slide relative to the base, a portion of the wick strip; clamping, with a slide configured to slide relative to the base, a portion of the heater around the portion of the wick strip; and releasing, with the holder, the support from the base.

The securing the support relative to the base of the example method may include locking the support in the holder.

The aligning the wick strip in the heater of the support of the example method may include inserting the wick strip into a channel in the guide plate.

The aligning the wick strip in the heater of the support may include inserting the wick strip into a gap defined by a channel in the guide plate and a retainer plate fixed to the guide plate.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1A is a front perspective view of an apparatus or fixture for assembling a heater assembly for a nicotine pod assembly according to at least one example embodiment.

FIG. 12 is a top view of an example embodiment of a wick sheet.

FIG. 13 is a top view of an example embodiment of a slicing guide used with the apparatus shown in FIG. 1A.

FIG. 14 is a top view of an example embodiment of a blade used with the slicing guide shown in FIG. 13.

DETAILED DESCRIPTION

Figure 1B:
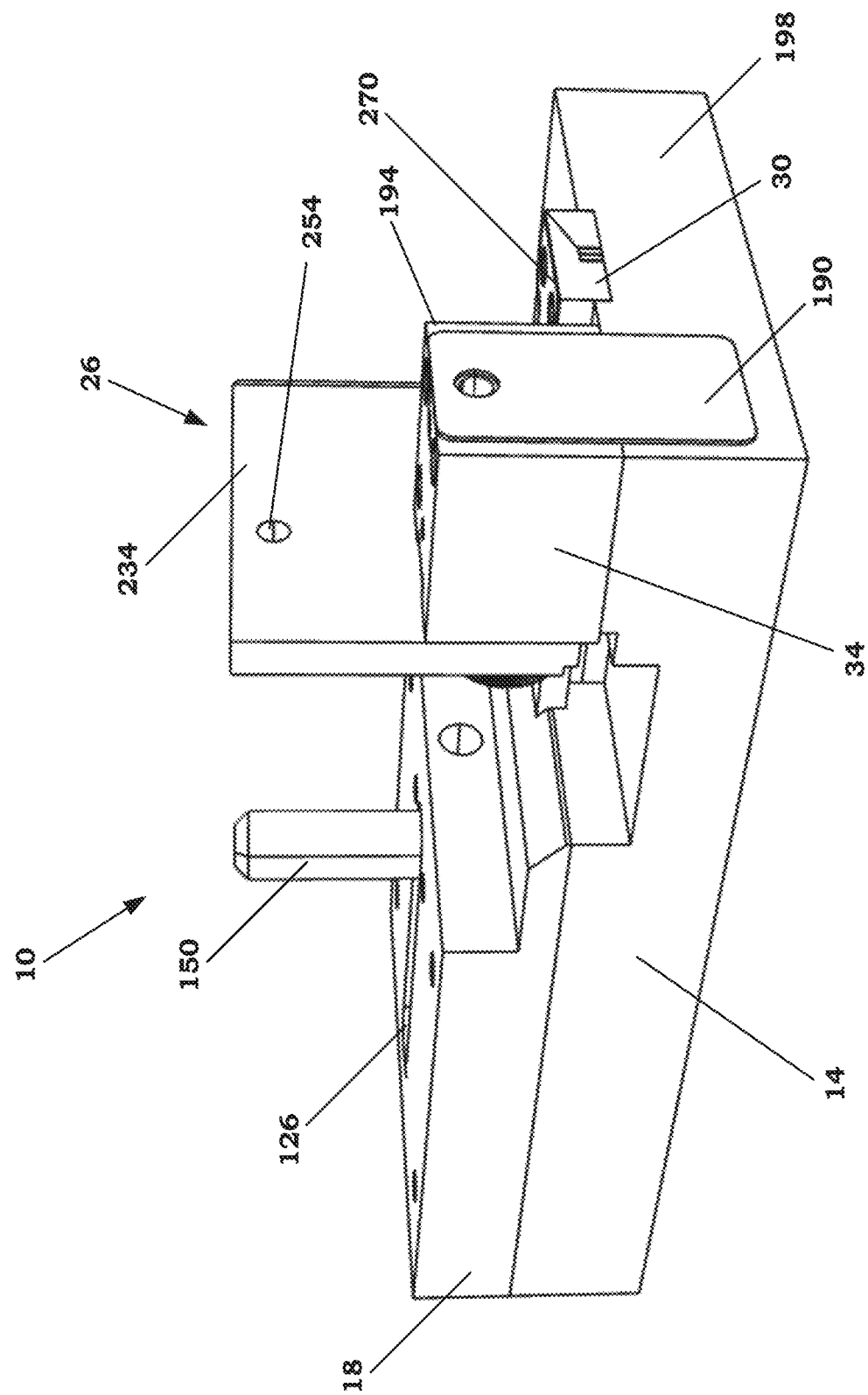
FIG. 1B is a rear perspective view of the apparatus shown in FIG. 1A.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

A nicotine electronic vaping device, or nicotine e-vaping device, includes a heating element that vaporizes a nicotine pre-vapor formulation to produce a nicotine vapor. The nicotine pre-vapor formulation may be enclosed in a housing or nicotine pod assembly. The nicotine electronic vaping device includes a power supply, such as a rechargeable battery, arranged in the device. The power supply is electrically connected to a heater assembly for the nicotine pod assembly. The power supply provides power to the heater assembly such that the heater assembly heats to a temperature sufficient to convert the nicotine pre-vapor formulation in the nicotine pod assembly to a nicotine vapor. The nicotine vapor exits the nicotine electronic vaping device through a mouthpiece including at least one outlet.

The nicotine pre-vapor formulation is a material or combination of materials that may be transformed into the nicotine vapor. For example, the nicotine pre-vapor formulation may include a liquid, solid, and/or gel formulation. These may include, for example and without limitation, water, oil, emulsions, beads, solvents, active ingredients, ethanol, plant extracts, nicotine, natural or artificial flavors, vapor formers such as glycerin and propylene glycol, and/or any other ingredients that may be suitable for vaping. During vaping, the nicotine electronic vaping device is configured to heat the nicotine pre-vapor formulation to generate a nicotine vapor. Nicotine vapor, nicotine aerosol, and nicotine dispersion are used interchangeably and refer to the matter generated or outputted by the devices disclosed, claimed, and/or equivalents thereof, wherein such matter contains nicotine. The nicotine e-vaping device may be regarded as an electronic nicotine delivery system (ENDS).

FIGS. 1A and 1B are front and rear perspective views of an apparatus or fixture for assembling a heater assembly for a nicotine pod assembly according to at least one example embodiment. The apparatus may be used in conjunction with the cutter illustrated in FIG. 10, in at least one example embodiment, and the slicing guide and blade illustrated in FIGS. 13 and 14, in at least one example embodiment, to prepare and assemble a heater assembly for a nicotine pod assembly as described herein.

Referring to FIGS. 1A and 1B, in at least one example embodiment, the apparatus, or fixture, 10 includes a base 14, a guide 18, a slide 22, a wick guide 26 (or nicotine wick guide), a holder 30, and a block 34.

Figure 3:
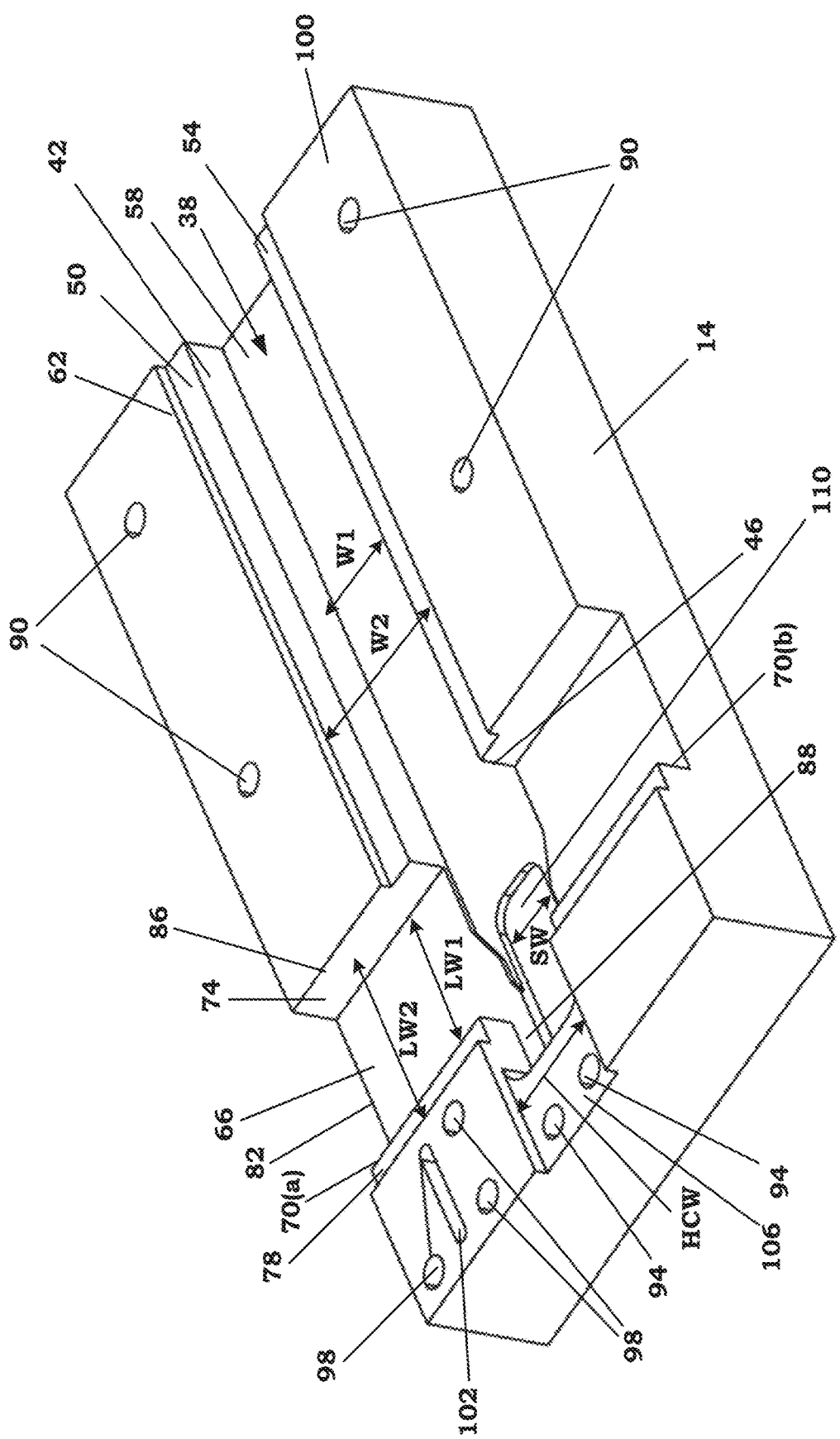
FIG. 3 is a perspective view of an example embodiment of a base of the apparatus shown in FIG. 1A.

In at least one example embodiment, a detailed illustration of the base 14 is shown in FIG. 3. The base 14 may include a longitudinal channel 38 with sidewalls 42, 46. Each sidewall includes a step 50, 54 that increases a width of the longitudinal channel 38. The longitudinal channel 38 may have a first width W1 at a base or bottom 58 of the longitudinal channel 38 and may have a second width W2 at a top 62 of the longitudinal channel 38 above the steps 50, 54, with the second width W2 being greater than the first width W1.

In the example embodiment shown in FIGS. 1A, 1B, and 3, for example, the base 14 may include a lateral channel 66 with sidewalls 70, 74 defining the lateral channel 66. The lateral channel 66 may extend orthogonal to and intersect the longitudinal channel 38. One of the sidewalls 70 of the lateral channel 66 may include a step 78, while the other of the sidewalls 74 is flat. The step 78 may increase a width of the lateral channel 66. The lateral channel 66 may have a first width LW1 at a bottom or base 82 of the lateral channel 66 and may have a second width LW2 at a top 86 of the lateral channel 66 above the step 78, with the second width LW2 being greater than the first width LW1.

The sidewall 70 may include a notch 88 at a position of the holder 30. Thus, the notch 88 may separate the sidewall 70 into two parts 70(a) and 70(b).

In the example embodiment shown in FIGS. 1A, 1B, and 3, for example, the base 14 may include a plurality of apertures 90, 94, 98 extending orthogonally through the base 14. Apertures 90 may receive a fastener (for example, a bolt, screw, or other fastener) for fixing the guide 18 on a top surface 100 the base 14. Apertures 94 may receive a fastener (for example, a bolt, screw, or other fastener) for fixing the holder 30 to the base 14. Apertures 98 may receive a fastener (for example, a bolt, screw, or other fastener) for fixing the block 34 to the base 14. A slot 102 may also be defined by the base 14 between the apertures 98. The slot 102 may receive a portion of the block 34.

The base 14 may additionally include a holder cutout 106 aligned with the longitudinal channel 38 and the apertures 94 for receiving the holder 30. The holder cutout 106 may correspond in width to a width of the holder 30, thus simplifying the assembly of the holder 30 on the base 14.

At an intersection between the longitudinal channel 38 and the lateral channel 66, a support cutout 110 may be defined by the base 14. The support cutout 110 may provide a track or guide for inserting a component of a heater assembly for a nicotine pod assembly into the holder 30. A width of the support cutout SW may be less than the width W1 of the longitudinal channel 38 and a width HCW of the holder cutout 106. The support cutout 110 may extend from the intersection between the longitudinal channel 38 and the lateral channel 66, beyond a plane of the sidewall 70, into notch 88, and to a section of the base 14 having the holder cutout 106.

Figure 2A:
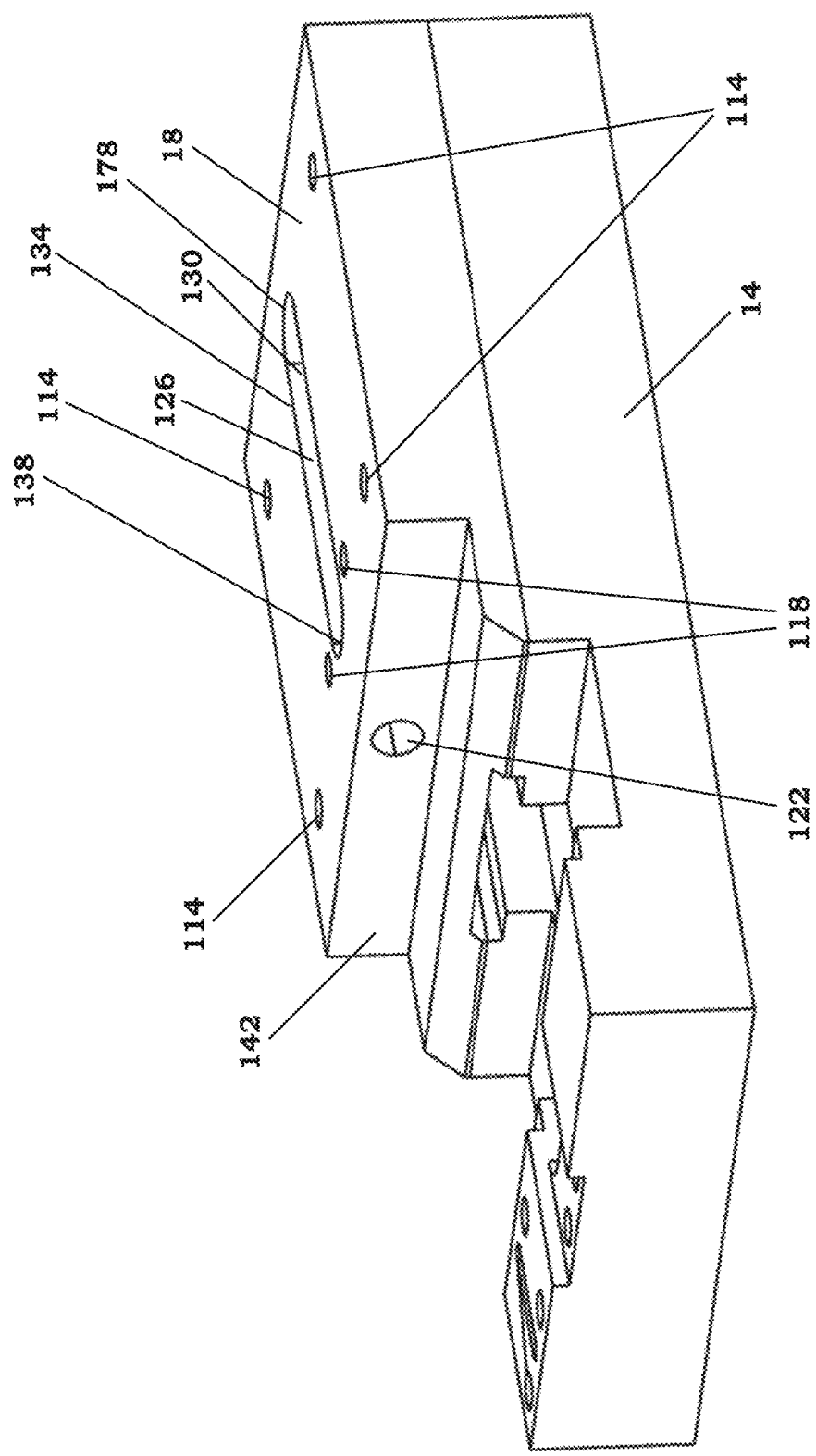
FIG. 2A is a perspective view of an example embodiment of an assembled base and guide of the apparatus shown in FIG. 1A.
Figure 2B:
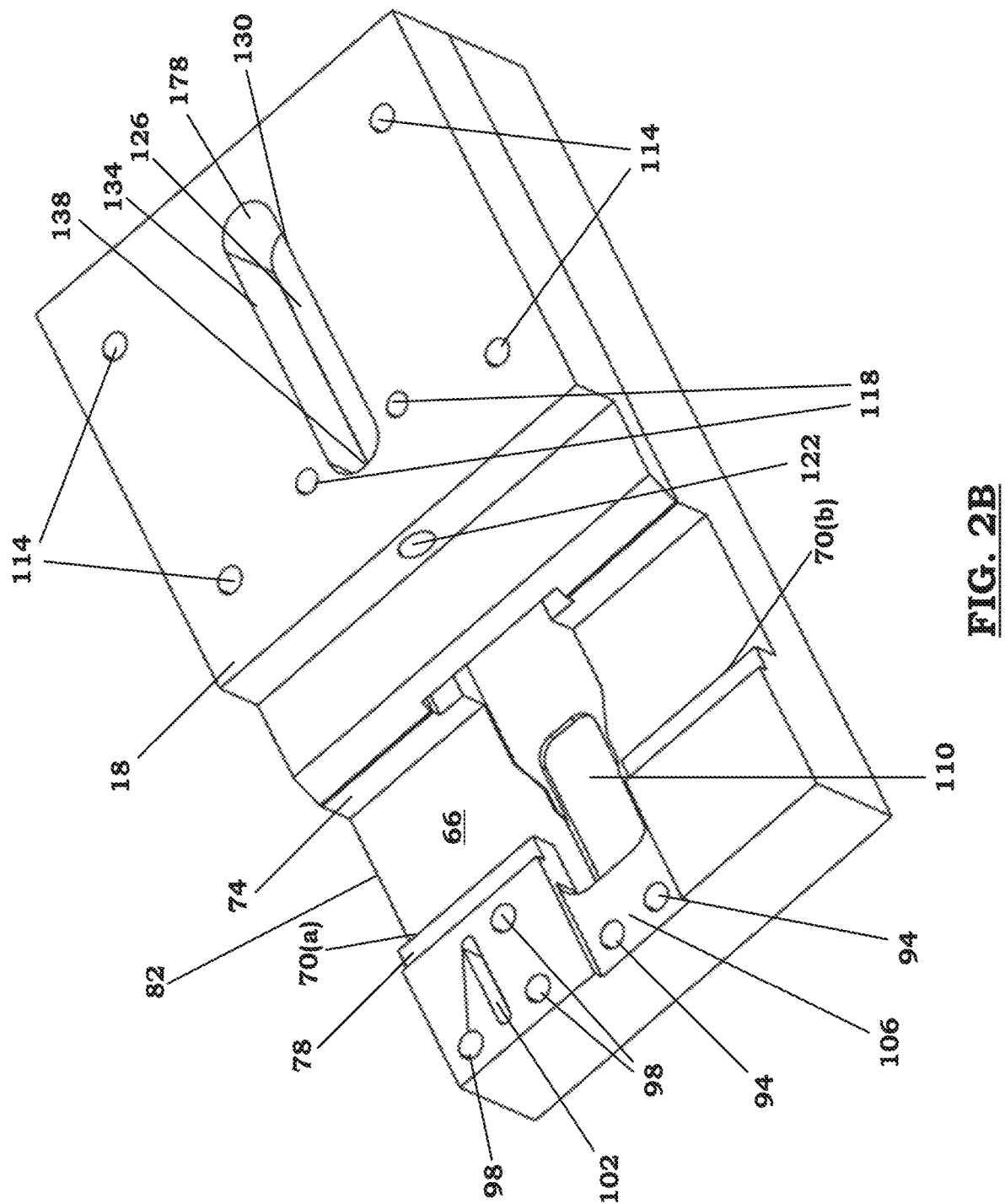
FIG. 2B is a top perspective view of the assembled base and guide shown in FIG. 2A.

FIGS. 2A and 2B are perspective views of an example embodiment of an assembled base 14 and guide 18 of the apparatus, or fixture, 10 shown in FIG. 1A. As previously mentioned, the guide 18 may be fixed to the base 14 at apertures 90 on the base 14. The guide 18 may include corresponding first apertures 114 that align with the apertures 90 in the base 14 and receive a fastener to fix the guide 18 to the base 14.

The guide 18 may include second apertures 118, a third aperture 122, and a slot 126. The slot 126 may be positioned longitudinally along a center of the guide 18 above the channel 38 in the base 14. The second apertures 118 may be positioned along each side 130, 134 and at a front end 138 of the slot 126. The second apertures 118 may receive pins, rods, or screws that extend through the second apertures 118 to apply light pressure on the slide 22 to ensure the motion of the slide 22 is controlled by the actuation of the pin 150. The third aperture 122 receive a pin, rod, or screw to set the functional travel distance of the slide 22 and may be positioned in a lateral center of a front face 142 of the guide 18 and extend through to the front end 138 of the slot 126.

Figure 4A:
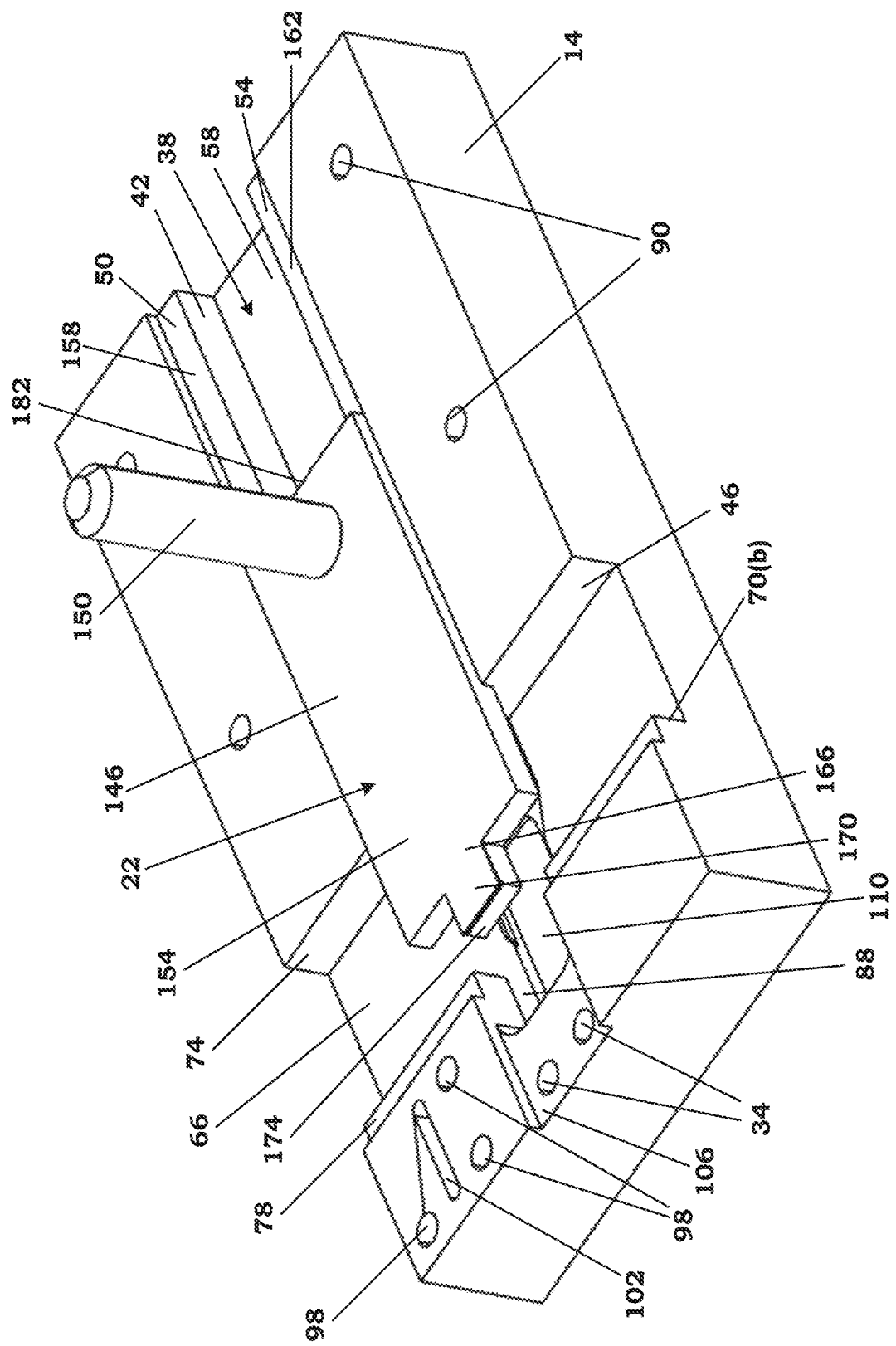
FIG. 4A is a perspective view of an example embodiment of an assembled base and slide of the apparatus shown in FIG. 1A.
Figure 4B:
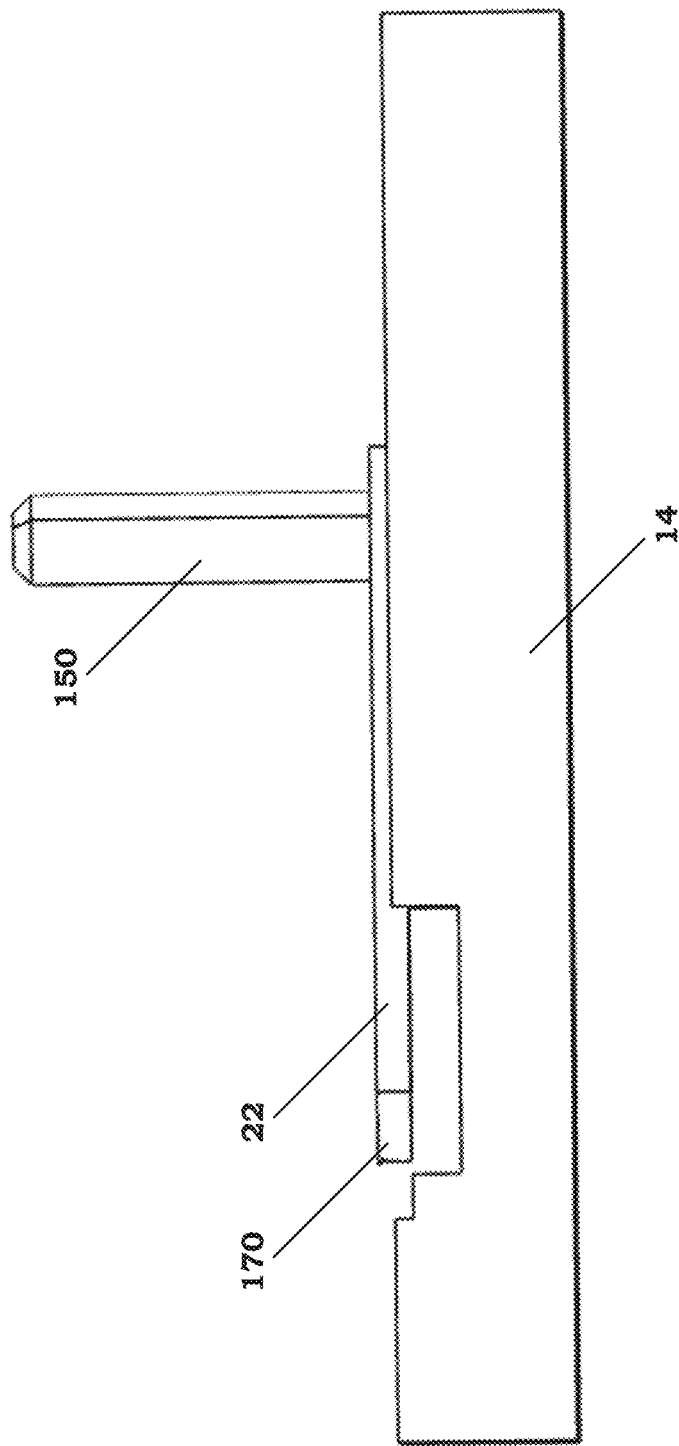
FIG. 4B is a side view of the assembled base and slide shown in FIG. 4A.

FIGS. 4A and 4B are perspective views of an example embodiment of an assembled base 14 and slide 22 of the apparatus, or fixture, 10 shown in FIG. 1A. The slide 22 is slideable within the longitudinal channel 38. The slide 22 may include a plate 146 and a pin 150 extending from a top surface 154 thereof. The plate 146 may rest and be slideable on a top surface 158, 162 of each step 50, 54. A front end 166 of the plate 146 may include a tab or projection 170 having a front face 174 that is slideable within the notch 88 in the base 14.

The pin 150 may extend orthogonally to the plate 146 and may be received within the slot 126 in the guide 18, as illustrated, for example, in FIGS. 1A and 1B. The slot 126 may serve as a guide track and stop for the pin 150. In a fully-forward position, the pin 150 is adjacent to (e.g., contacts) the front end 138 of the slot 126 and a plane along the front face 174 of the tab 170 on the slide 22 aligns with a plane along the sidewall 70 of the lateral channel 66. In a fully-rearward position, the pin 150 is adjacent to (e.g., contacts) a rear end 178 of the slot 126 and a plane along a rear face 182 of the plate 146 of the slide 22 aligns with a plane along a rear face 186 of the base 14.

Figure 5:
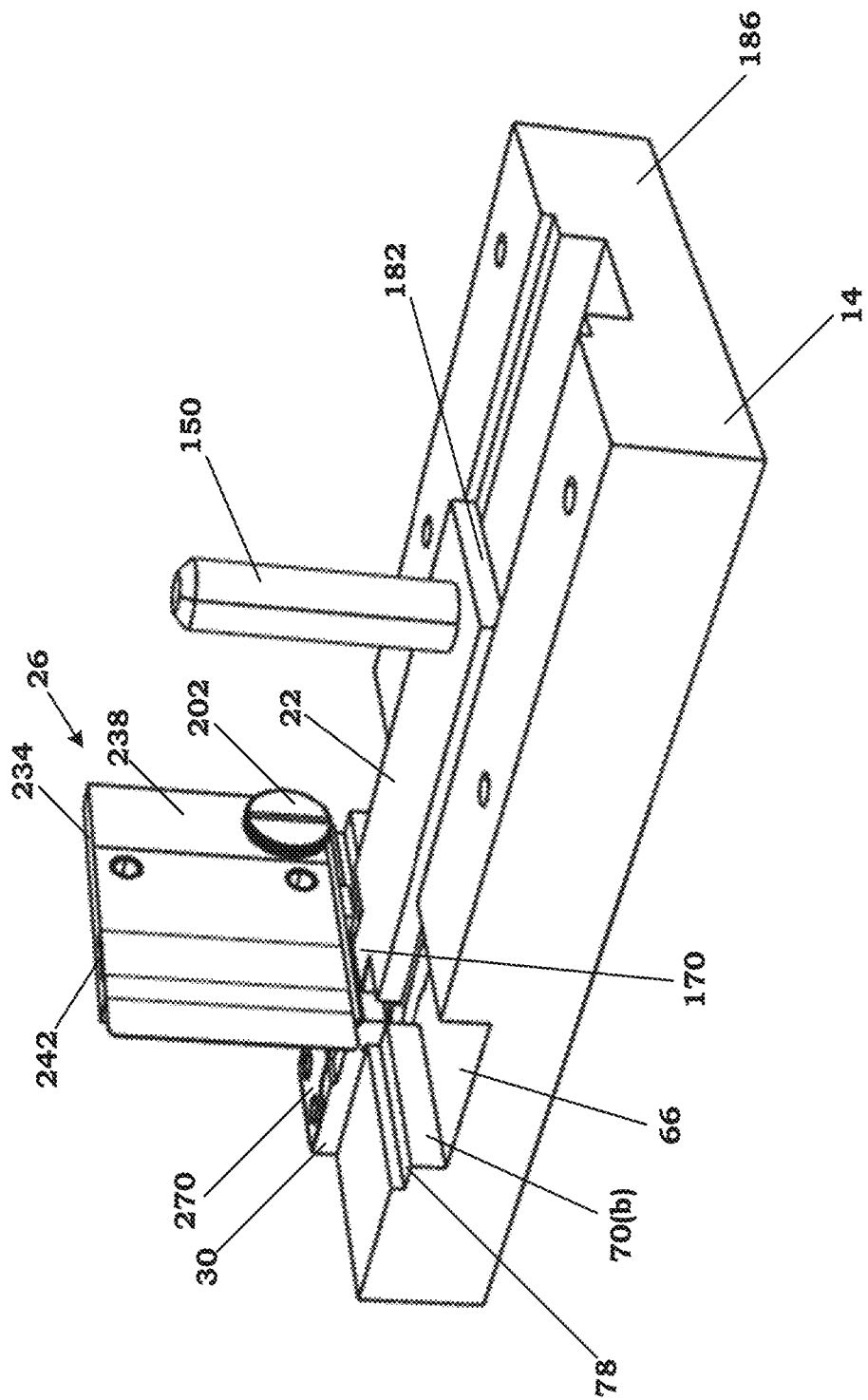
FIG. 5 is a perspective view of an example embodiment of the apparatus shown in FIG. 1A with the guide removed.

Referring to FIG. 5, a perspective view of an example embodiment of the apparatus, or fixture, 10 shown in FIG. 1A with the guide removed is illustrated. As shown in FIGS. 1A, 1B, and 5, for example, the wick guide 26 may be fixed on the base 14 by block 34. As previously stated, block 34 may be secured to the base 14 at apertures 98 by fasteners and at slot 102. Additionally, a retract spring 190 may be fixed to an outer, forward face 194 of block 34 and a forward face 198 of base 14, causing a plane along forward face 194 to align with a plane along forward face 198 and restrict movement of the forward face 194 of block 34 from protruding beyond the forward face 198 of base 14.

The wick guide 26 may be fixed to the block 34 by a fastener, such as a shoulder screw, 202, as illustrated in FIGS. 1A and 8A-9B, for example. In some example embodiments, the fastener 202 (FIG. 8C) may include a top 206 and a body 210 having a smooth portion 214 and a threaded portion 218. The threaded portion 218 may engage with threads in an aperture 222 in block 34 (FIG. 8B). The aperture 222 may be a counter-sunk aperture having a large-diameter portion 226 that mates with part of the smooth portion 214 of the fastener 202 and a small-diameter portion 230 that is threaded and mates with the threaded portion 218 of the fastener 202. The top 206 of the fastener 202 may be knurled, slotted, or knurled and slotted for easy insertion and removal from the aperture 222.

Figure 9B:
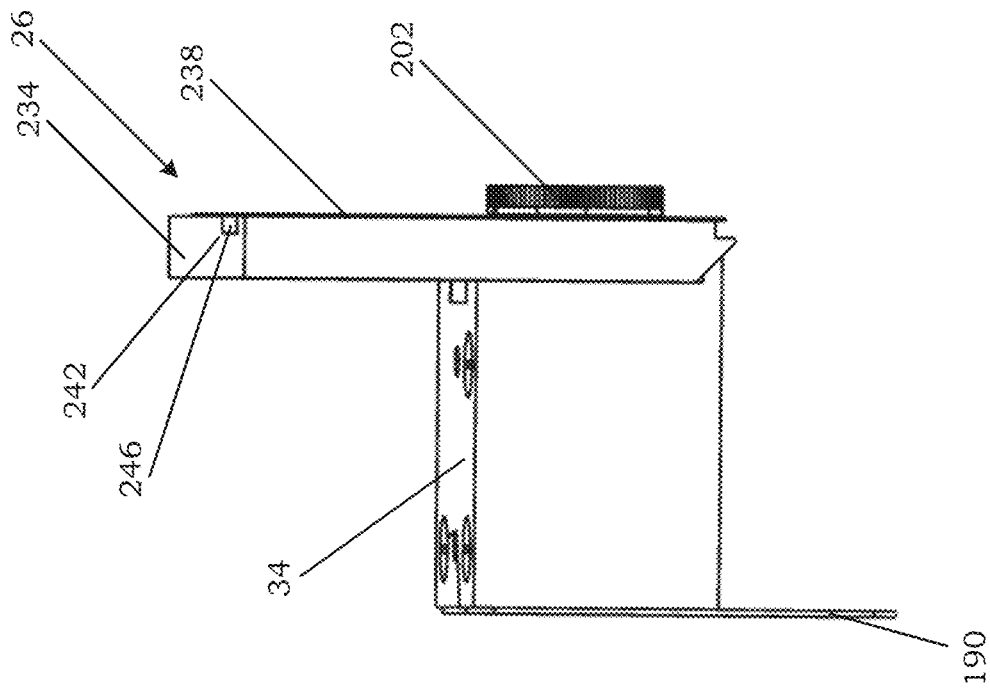
FIG. 9B is a side view of the wick guide shown in FIG. 9A.
Figure 9A:
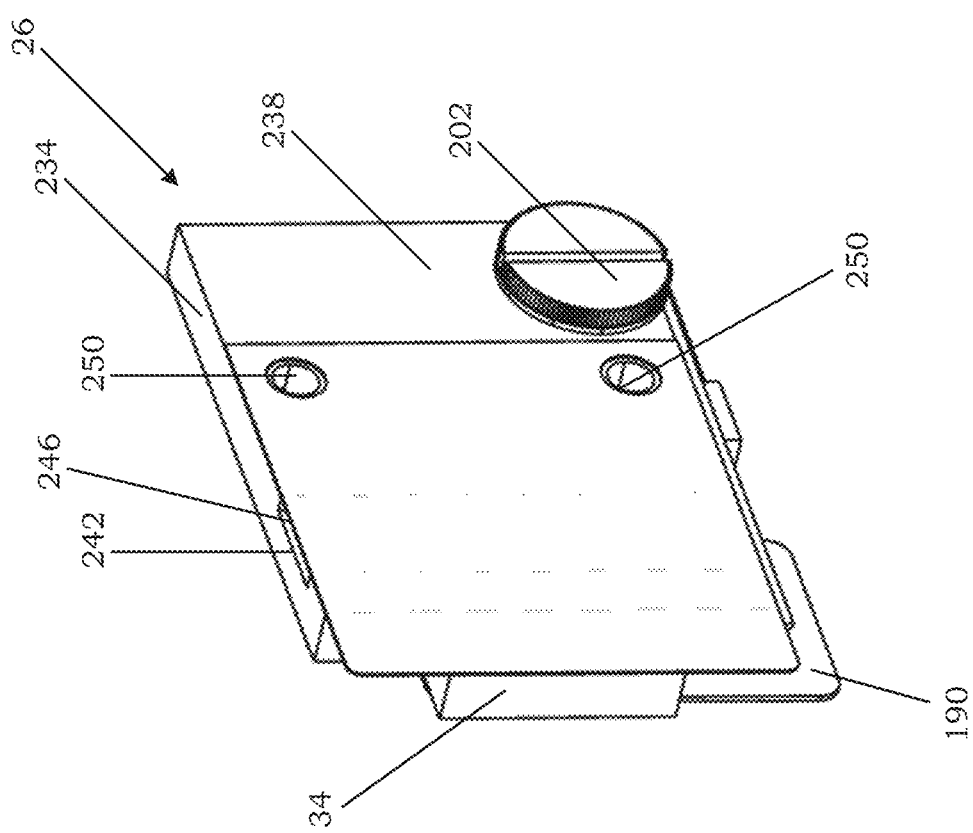
FIG. 9A is a front perspective view of an example embodiment of a wick guide of the apparatus shown in FIG. 1A.

The wick guide 26, as illustrated in example embodiments of FIGS. 9A and 9B, may include a wick feed 234 (or nicotine wick feed) and a wick retainer 238 (or nicotine wick retainer). The wick feed 234 may be a plate, or channeled plate, having a channel or slot 242 formed therein. The channel 242 may extend across a width of the wick feed 234 and may be a width sufficient to accommodate a wick configured to draw a nicotine pre-vapor formulation via capillary action (discussed in further detail below). For example, the channel 242 may have a width within a range of 0.0625 inches to 1 inch, and more specifically within a range of 0.125 inches and 0.5 inches. Although an example width is provided, it is understood that the width of the channel 242 may be sized differently to fit various sized wicks configured to draw a nicotine pre-vapor formulation via capillary action.

The wick retainer 238 may be a flat plate that aligns with (and is fixed to) the wick feed 234 to define a guide or track 246 with the channel 242 in the wick feed 234 in which the wick for nicotine wicking is inserted during assembly (discussed in further detail below). The wick retainer 238 may include apertures 250 that align with apertures 254 (FIG. 1B) in the wick feed 234 which receive fasteners therein to fix the wick retainer 238 to the wick feed 234. A fastener or pin extending through one of the apertures 250 may extend beyond the wick feed 234 and fit within a track 258 in block 34, thereby allowing the wick feed 234 to pivot relative to the block 34. Additionally, the smooth portion 214 of the fastener 202 is received within an aperture in the wick guide 26, providing a pivot point around which the wick guide 26 may rotate.

Figure 6:
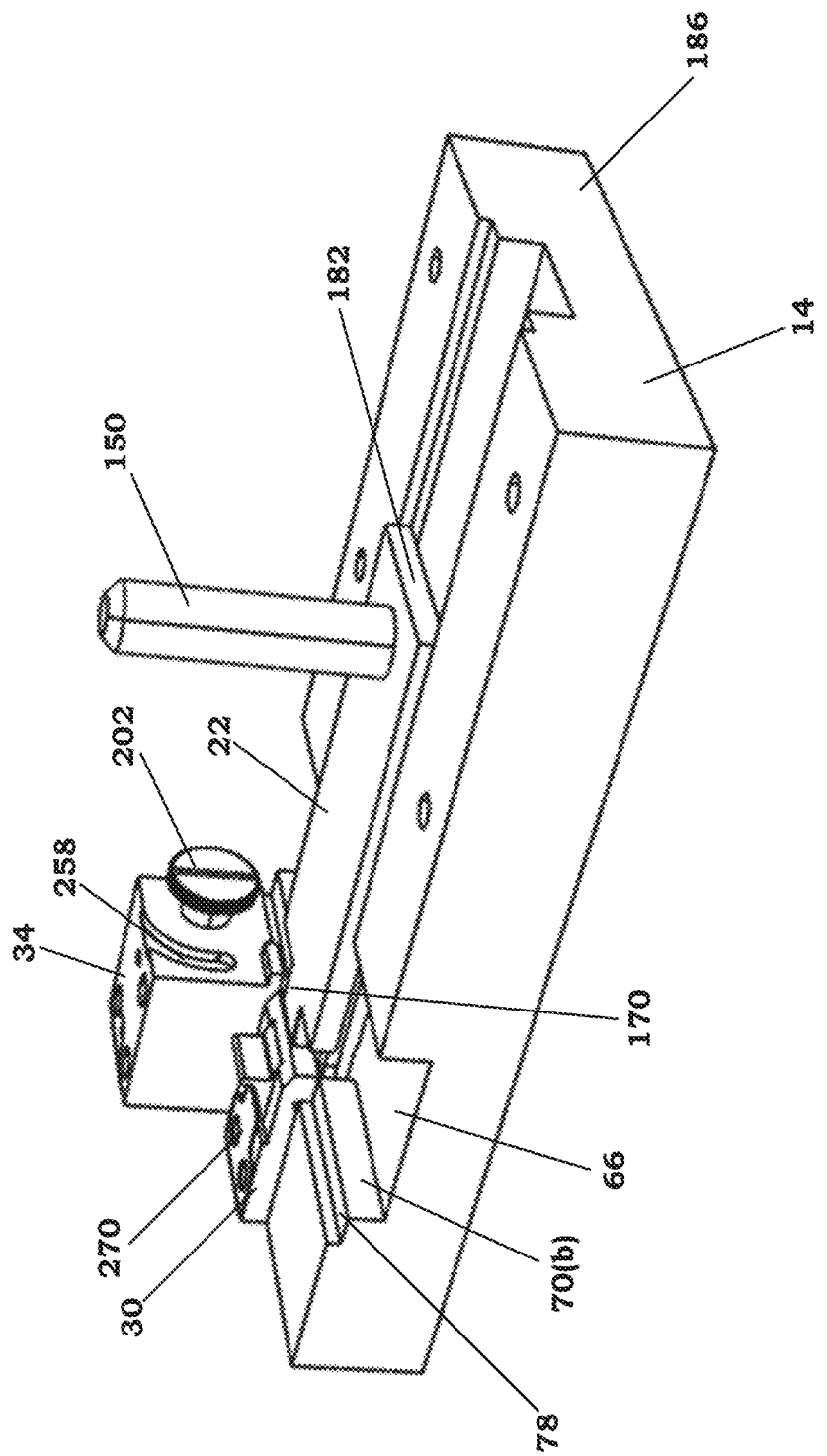
FIG. 6 is a perspective view of an example embodiment of the apparatus shown in FIG. 1A with the guide, wick feed, and wick retainer removed.
Figure 7B:
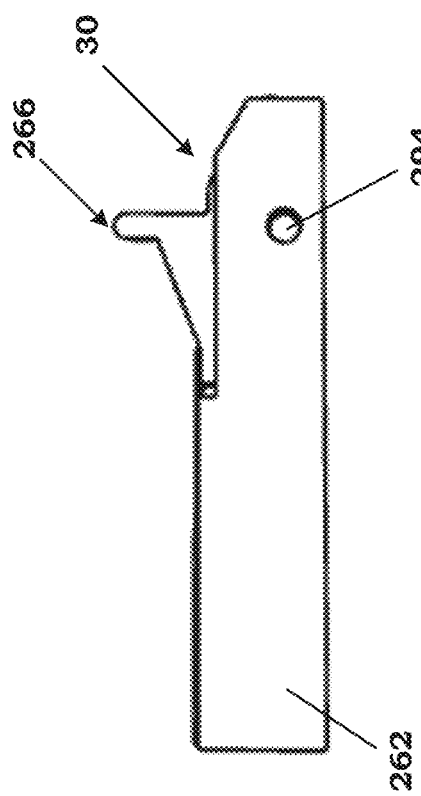
FIGS. 7A-7D are perspective, side, top, and rear views, respectively, of an example embodiment of a holder of the apparatus shown in FIG. 1A.
Figure 7D:
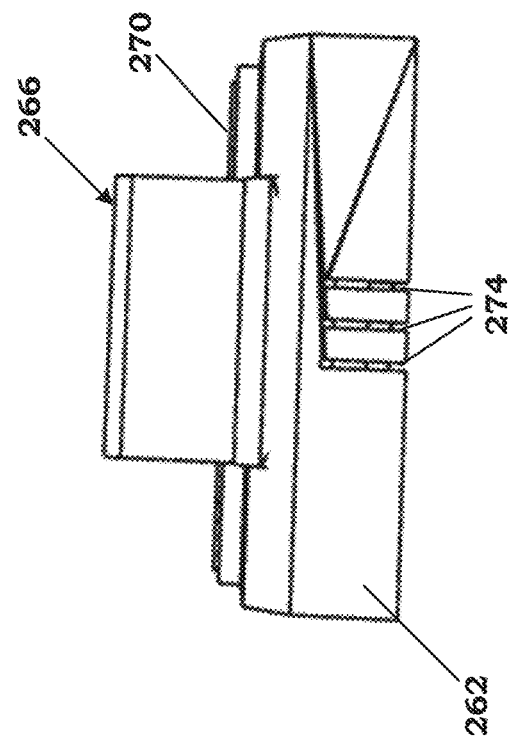
Figure 7A:
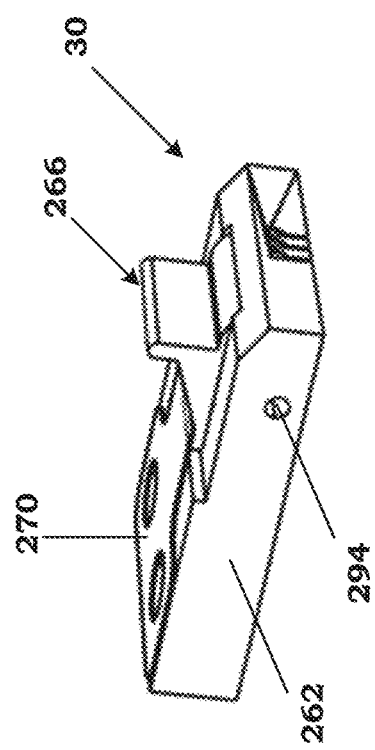
Figure 7C:
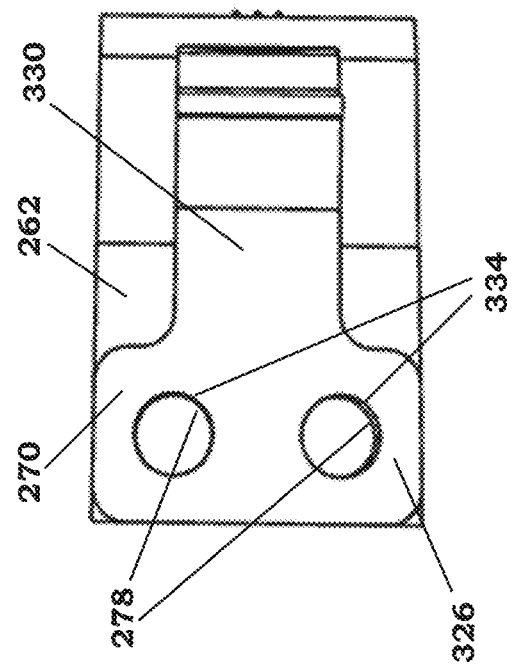
Figure 7F:
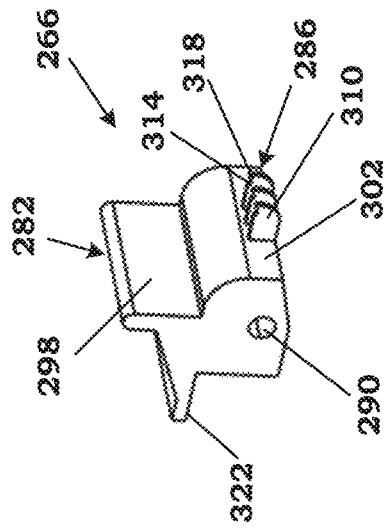
FIG. 7F is a perspective view of an example of a lock of the holder shown in FIGS. 7A-7E.
Figure 7E:
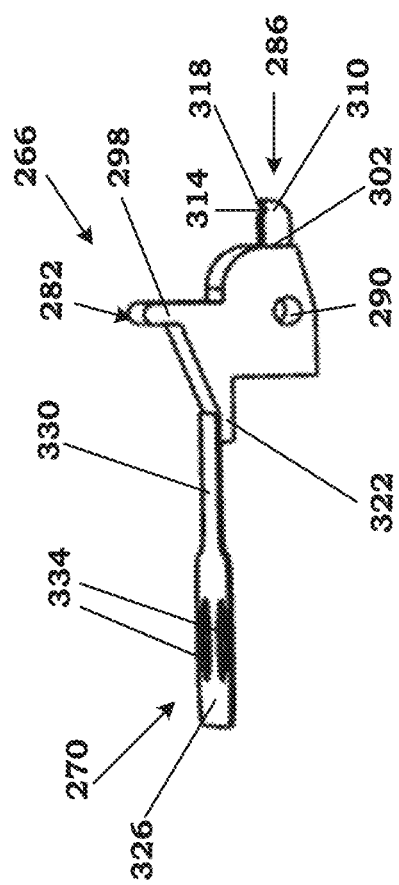
FIG. 7E is a side view of an example embodiment of a lock and spring of the holder shown in FIGS. 7A-7D.
Figure 8A:
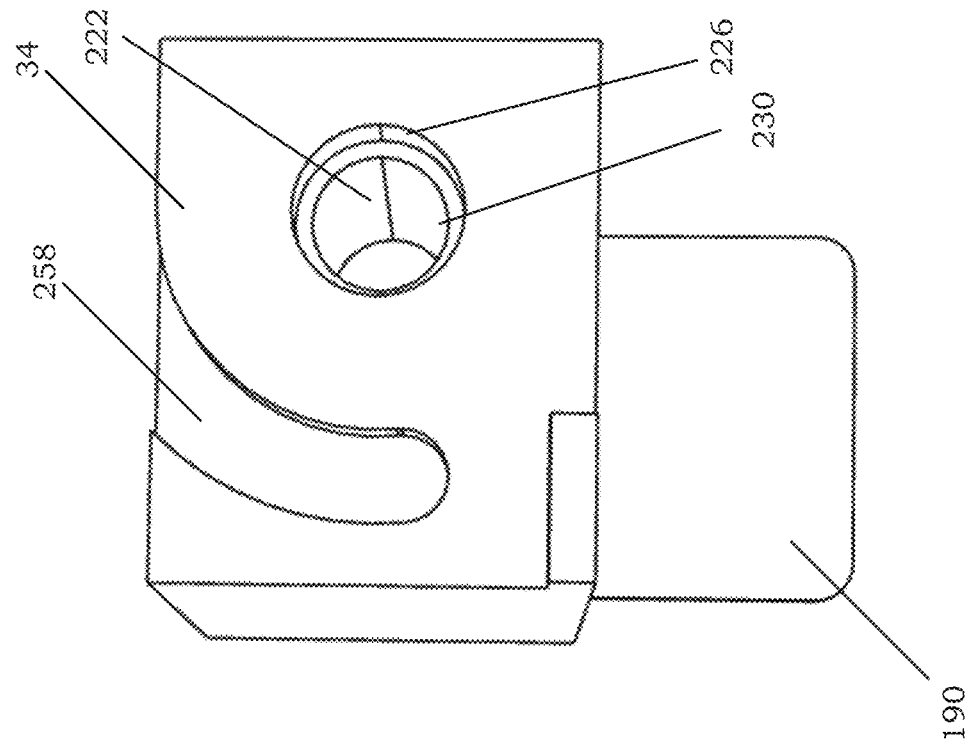
FIG. 8A is a front perspective view of an example embodiment of a fixture assembly of the apparatus shown in FIG. 1A.
Figure 8B:
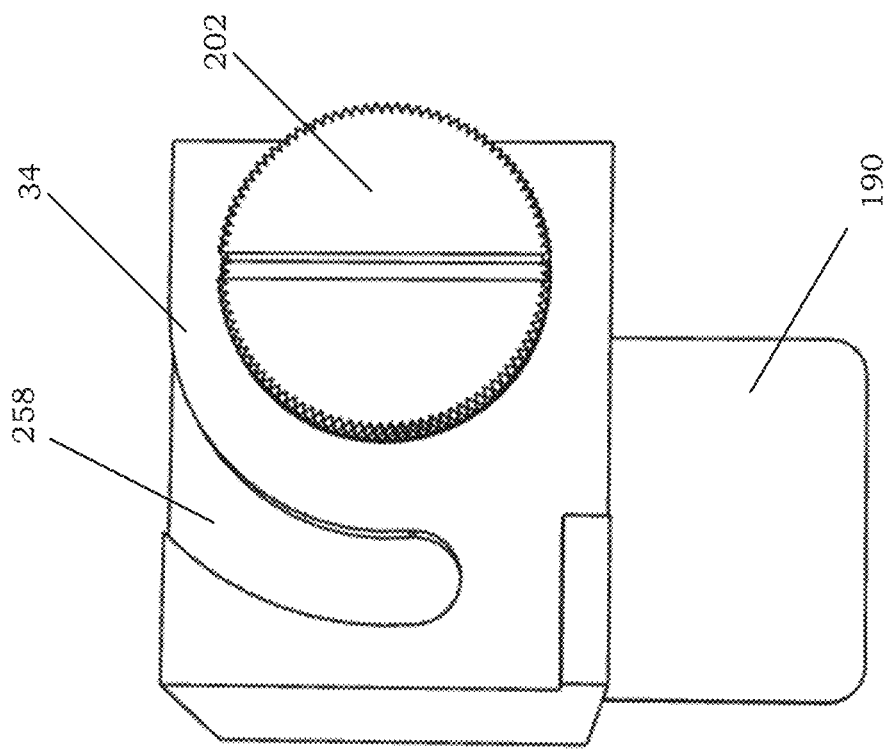
FIG. 8B is a front perspective view of an example embodiment of a block and spring of the fixture assembly shown in FIG. 8A.
Figure 8D:
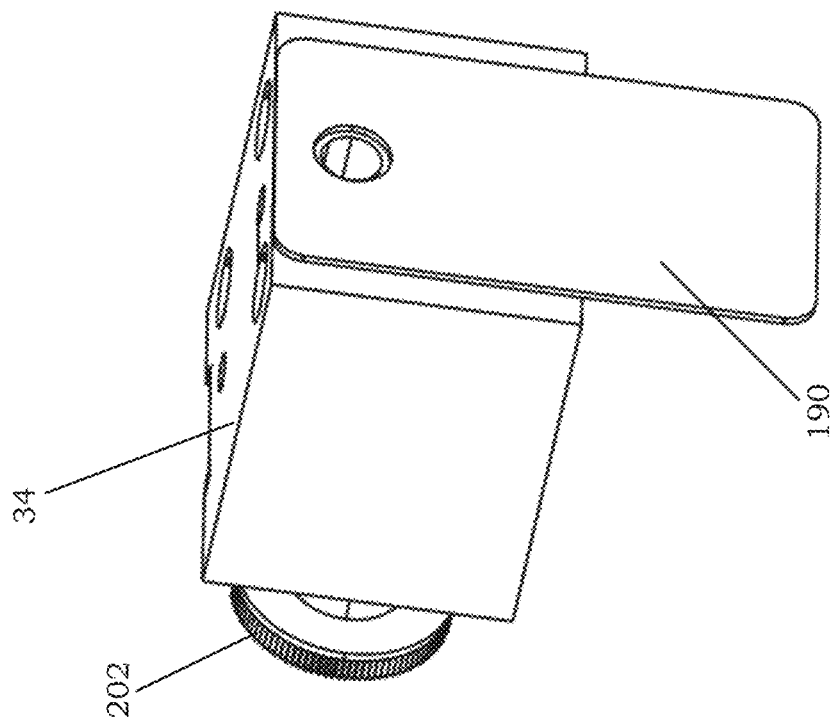
FIG. 8D is a rear perspective view of the fixture assembly shown in FIG. 8A.
Figure 8C:
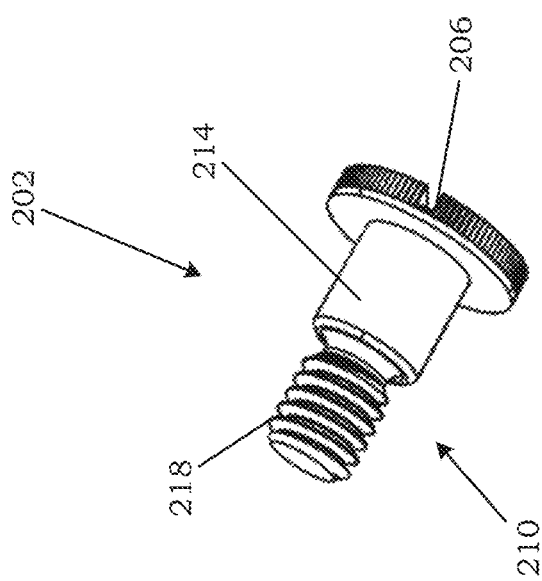
FIG. 8C is a perspective view of an example embodiment of a fastener of the fixture assembly shown in FIG. 8A.

FIGS. 6-7F illustrate detailed views of an example embodiment of the holder of the apparatus, or fixture, 10 shown in FIG. 1A. The holder 30 may include a base 262, a lock 266, and a resilient member 270 (e.g., spring). The base 262 may further include slots 274 for receiving one or more fingers of a heater assembly for a nicotine pod assembly (further described below) and/or portions of the lock 266. The base 262 may also include apertures 278 configured to align with apertures 94 in the base 14 and receive fasteners to fix the holder 30 to the base 14.

In some example embodiments, the lock 266 may further include a toggle 282 and at least one locking finger 286. The lock 266 may be rotatably fixed to the base 262 at apertures 290 in the toggle 282. Apertures 290 in the toggle 282 may align with apertures 294 in the base 262 to receive a rod or pin therein. The rod or pin may provide a pivot point about which the toggle 282 may rotate. The toggle 282 may include a projection or lever 298 configured to be manipulated by an assembly technician to move the toggle 282 between a first, forward position and a second, rearward position. In the first position, the locking fingers 286 may be in an open, or unlocked, position (further described below), and in the second position, the locking fingers 286 may be in a closed, or locked, position (further described below).

The locking fingers 286 may be fixed to a front face 302 of the toggle 282 and may rotate with the rotation of toggle 282. In some example embodiments, three locking fingers 286 may be fixed to the toggle 282. However, it is understood that any number of locking fingers 286 may be included. In some example embodiments, each of the locking fingers 286 may be a plate including a rectangular body 306 and a hook 310 (FIG. 7F). The hook 310 may be defined by a dip 314 and a point 318.

A tab 322 on an opposite side of the toggle 282 from the front face 302 contacts the resilient member 270 (e.g., a spring). The resilient member 270 is a flat, plate-like spring having a body 326 and a tab or projection 330 extending from the body 326. The body 326 of the resilient member 270 is fixed to the base 262 at apertures 334 by fasteners (for example only, screws or bolts). Apertures 334 align with apertures 278 in the base 262 and are configured to receive the fasteners. The tab 330 extends similar to a cantilever beam and overlays the tab 322 of the toggle 282. The tab 330 of the resilient member 270 provides a counter force on the toggle 282 to bias the toggle 282 in the second, rearward, position such that the locking fingers 286 are biased in the locked, closed, position.

Figure 10:
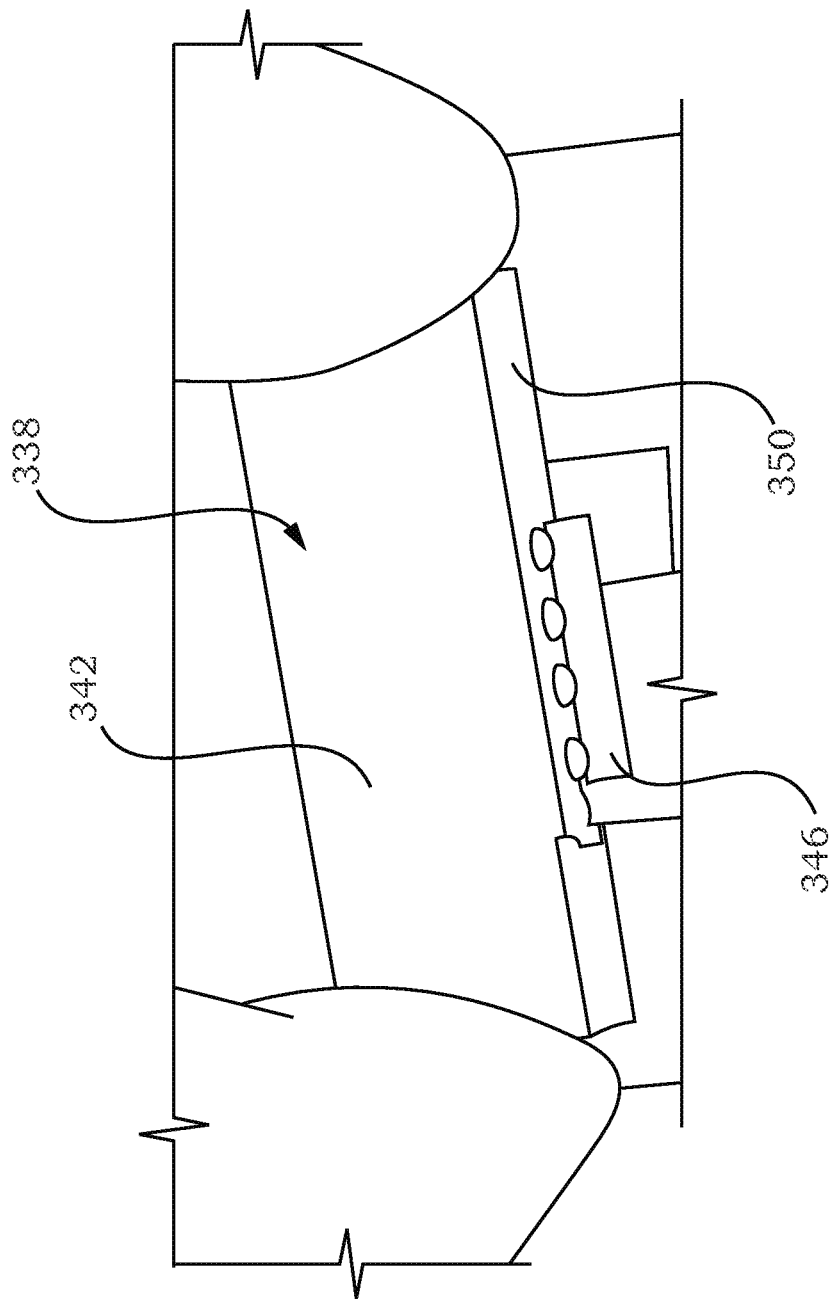
FIG. 10 is a perspective view of an example embodiment of a cutter used with the apparatus shown in FIG. 1A.
Figure 11:
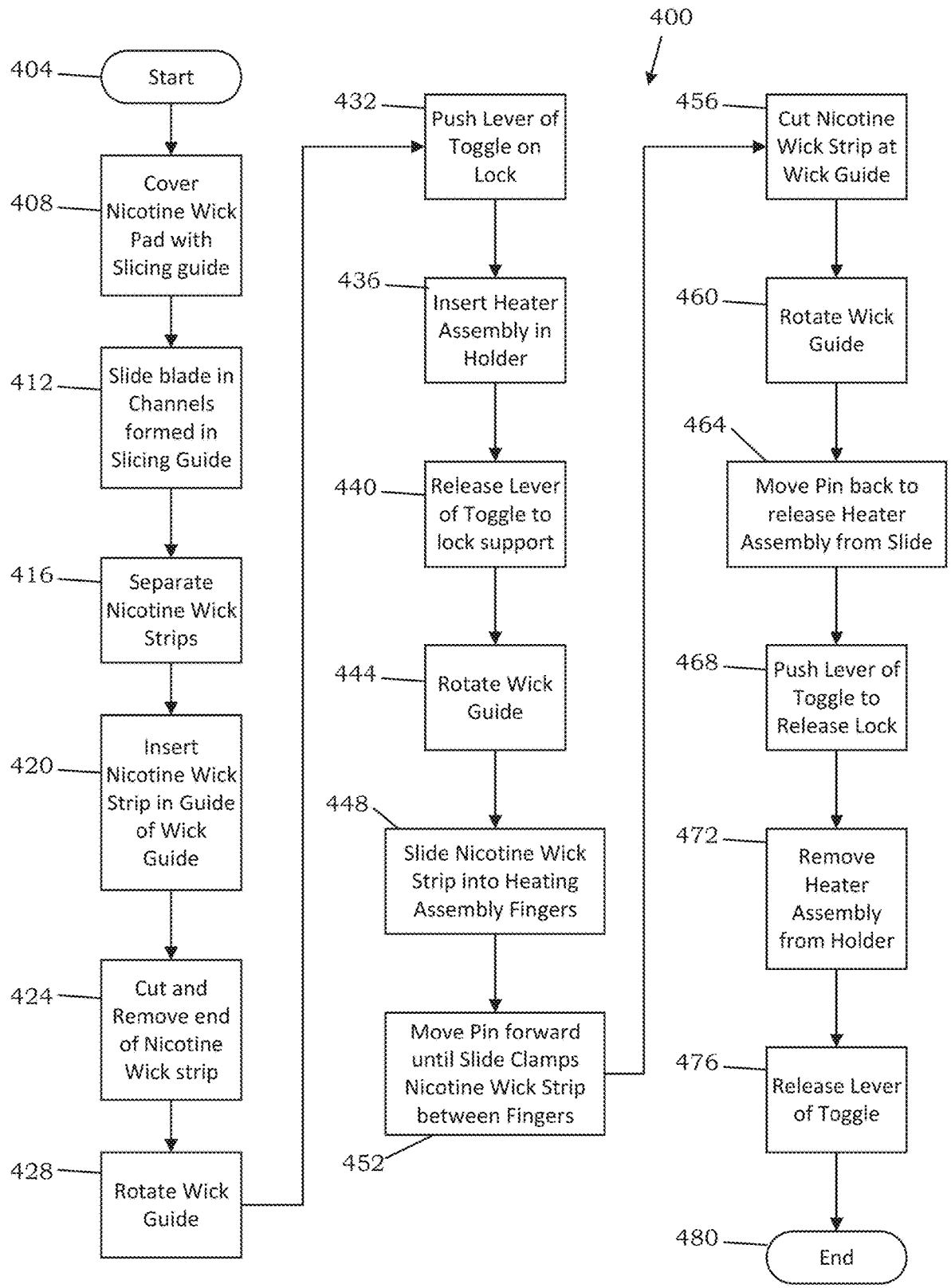
FIG. 11 is a flow chart for at least one example embodiment of a method of preparing and assembling a heater assembly for a nicotine pod assembly.

FIG. 10 is a perspective view of an example embodiment of a cutter 338 that may be used with the apparatus, or fixture, 10 shown in FIG. 1A. The cutter 338 includes a block 342 and a blade 346. The blade 346 may be positioned on a front face 350 of the block 342. In some embodiments, the blade 346 may be fixed to the block 342 by one or more fasteners.

The cutter 338 may be slideable along the top surface 154 of the slide 22 from a first position to a second position. In the first position, the cutter 338 may be disposed on the top surface 154 of the slide 22 between the wick guide 26 and the guide 18. In the second position, the cutter 338 may be disposed on the top surface 154 of the slide 22 with the blade 346 disposed adjacent the holder 30 and under the wick guide 26.

Still referring to the example embodiment shown in FIGS. 1-10, the apparatus, or fixture, 10 and cutter 338 may be used in a method 400 of preparing and assembling a heater assembly for a nicotine pod assembly. Method 400 may start at 404. At step 408, a wick pad 500 (FIG. 12) is covered by a slicing guide 504 (FIG. 13). For example, the slicing guide 504 may be set on the wick pad 500.

In at least one example embodiment, the wick pad 500 (or nicotine wick pad) may include filaments (or threads) having a capacity to draw the nicotine pre-vapor formulation via capillary action. For example, the wick pad 500 may be a sheet of glass (or ceramic) fibers or filaments woven together. In at least one example embodiment, the wick pad 500 may include any suitable material or combination of materials. Examples of suitable materials may be, but not limited to, glass, ceramic-based, or graphite-based materials.

The wick pad 500 may have any suitable capillary drawing action to accommodate nicotine pre-vapor formulations having different physical properties such as density, viscosity, surface tension and vapor pressure. The capillary drawing action is the movement of the nicotine pre-vapor formulation (e.g., liquid with nicotine and other substances dissolved therein) within the spaces of the porous wick pad 500 material due to the forces of adhesion, cohesion, and surface tension. Capillary action occurs when molecules of a liquid stay close together (cohesion) while being attracted to and adhering to internal surfaces of a porous structure (adhesion). Notably, capillary action occurs when the adhesion of the molecules of the liquid to the wall of the structure is stronger than the cohesive forces between the molecules. Because the nicotine pre-vapor formulation may include various substances (such as, without limitation water, oil, emulsions, beads, solvents, active ingredients, ethanol, plant extracts, nicotine, natural or artificial flavors, vapor formers such as glycerin and propylene glycol, and/or any other ingredients that may be suitable for vaping, as previously mentioned), a wicking material structured to draw the nicotine pre-vapor formulation may be designed for the specific formulation. Therefore, the material of the wick pad 500 may have a different structure and/or compound to promote capillary action for a specific nicotine pre-vapor formulation. For example, the diameter of the pores and/or dimension of the interstitial spaces in the wick pad 500 material may be sized appropriately to facilitate the drawing of the nicotine pre-vapor formation via capillary action based on the physical properties of the formulation (e.g., surface tension) and the material (e.g., hydrophilicity). For example, a size of the capillary space may need to increase as a density of the liquid increases. Additionally, in an example embodiment, the wick pad 500 may be non-conductive.

Although the example wick pad 500 is illustrated as a circular sheet in FIG. 12, it is understood that the wick pad 500 may take any shape, to include a rectangular sheet, a square sheet, or any other-shaped sheet.

As illustrated in FIG. 13, the example slicing guide 504 may include one or more slots or channels 508 penetrating a thickness thereof. Each of the channels 508 may extend in a length direction of the slicing guide 504 and may be aligned in a width direction of the slicing guide 504. The channels 508 may be evenly spread in the width direction, so that when the wick pad 500 is cut or divided, equal width strips are created.

An aperture 512 may be on one end of each channel 508. In some embodiments, the aperture 512 may be on alternating ends of the channels 508. The aperture 512 on the end of the channel 508 may facilitate insertion of a blade 516 (further described below). With the aperture 512 on alternating ends of the channels 508, the blade 516 may be inserted and sliced through each channel in a more efficient manner.

Figure 16A:
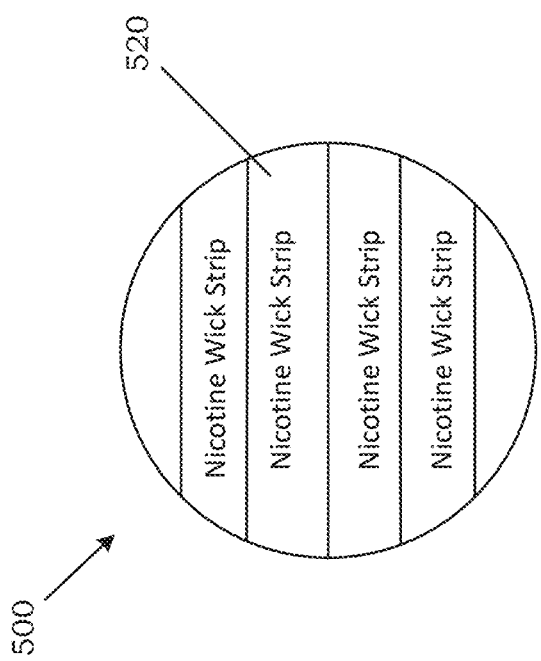
FIG. 16A is a top view of an example embodiment of a sliced wick sheet.

At step 412, the blade 516, or razor, is sliced through each channel 508 in the slicing guide 504 to cut or divide the wick pad 500 into wick strips 520 (FIG. 16A). In an example embodiment illustrated in FIG. 14, the blade 516 may include a cutting edge 522 and a grip 526. The cutting edge 522 may be a sharp edge used to cut or divide the wick pad 500 into wick strips 520 (or nicotine wick strips). The grip 526 may be for example, a dulled edge of the blade 516 or an overlay on an edge of the blade 516 opposite the cutting edge 522 to provide a portion of the blade 516 for an assembly technician to grasp.

Figure 15B:
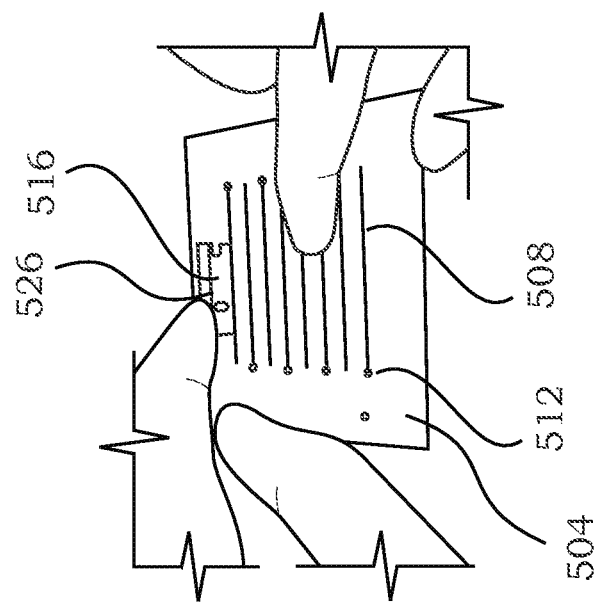
FIGS. 15A-15B illustrate an example embodiment of a method of slicing a wick sheet using the slicing guide shown in FIG. 13 and the blade shown in FIG. 14.
Figure 15A:
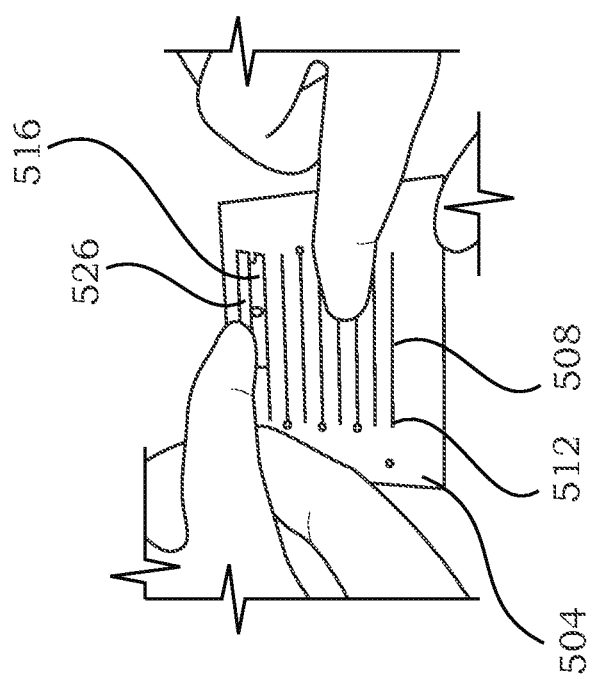

As illustrated in FIGS. 15A and 15B, the cutting edge 522 of the blade 516 is inserted into the aperture 512 of each channel 508 of the slicing guide 504 and passed, or sliced, through the length of the channel 508. This movement of the blade 516 cuts or separates the wick pad 500 positioned beneath the slicing guide 504. The blade 516 is then moved to the next channel 508 until a slice has been made in each channel 508 of the slicing guide 504.

Figure 16B:
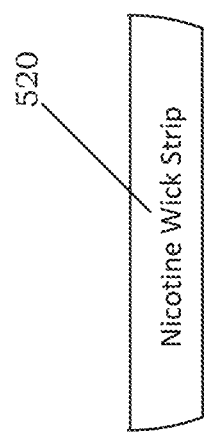
FIG. 16B is a top view of an example embodiment of a wick strip from the sliced wick sheet shown in FIG. 16A.

At step 416, the slicing guide 504 is removed and the wick strips 520 are separated from the wick pad 500. As illustrated in FIGS. 16A and 16B, when the slicing guide 504 is removed from the wick pad 500, the wick pad 500 is divided into a plurality of wick strips 520 corresponding to the position of the channels 508. Each wick strip 520 may be separated from the adjacent strips 520.

Figure 17A:
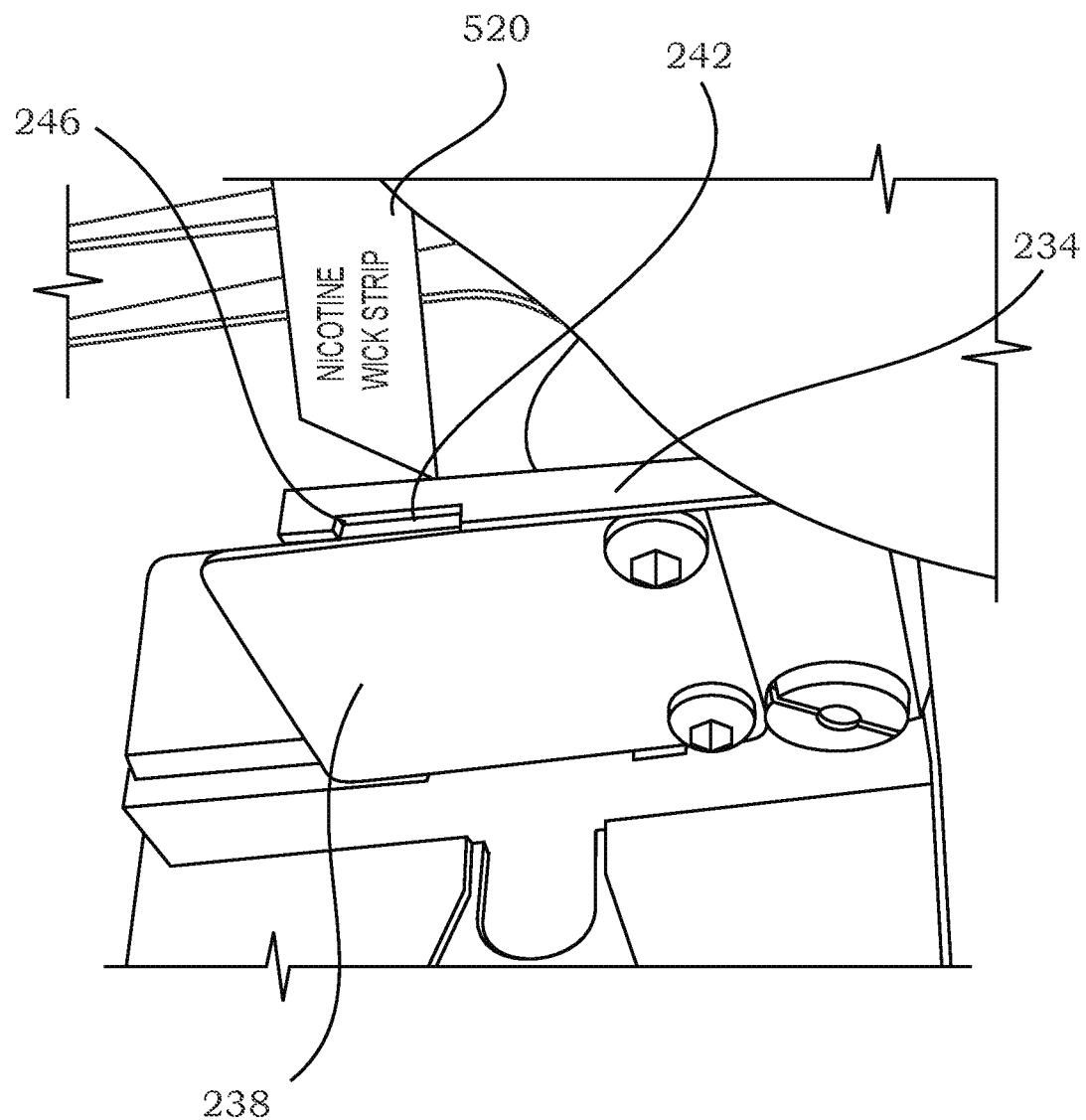
FIG. 17A illustrates an example embodiment of a method of inserting the wick strip shown in FIG. 16B into a channel of the wick guide shown in FIGS. 9A-9B.

At step 420, the wick strip 520 is inserted in the guide or track 246 of the wick guide 26. As illustrated in FIG. 17A, the width of the channel 242 defining the guide or track 246 is slightly larger than the width of the wick strip 520 to accommodate and guide the wick strip 520.

Figure 17B:
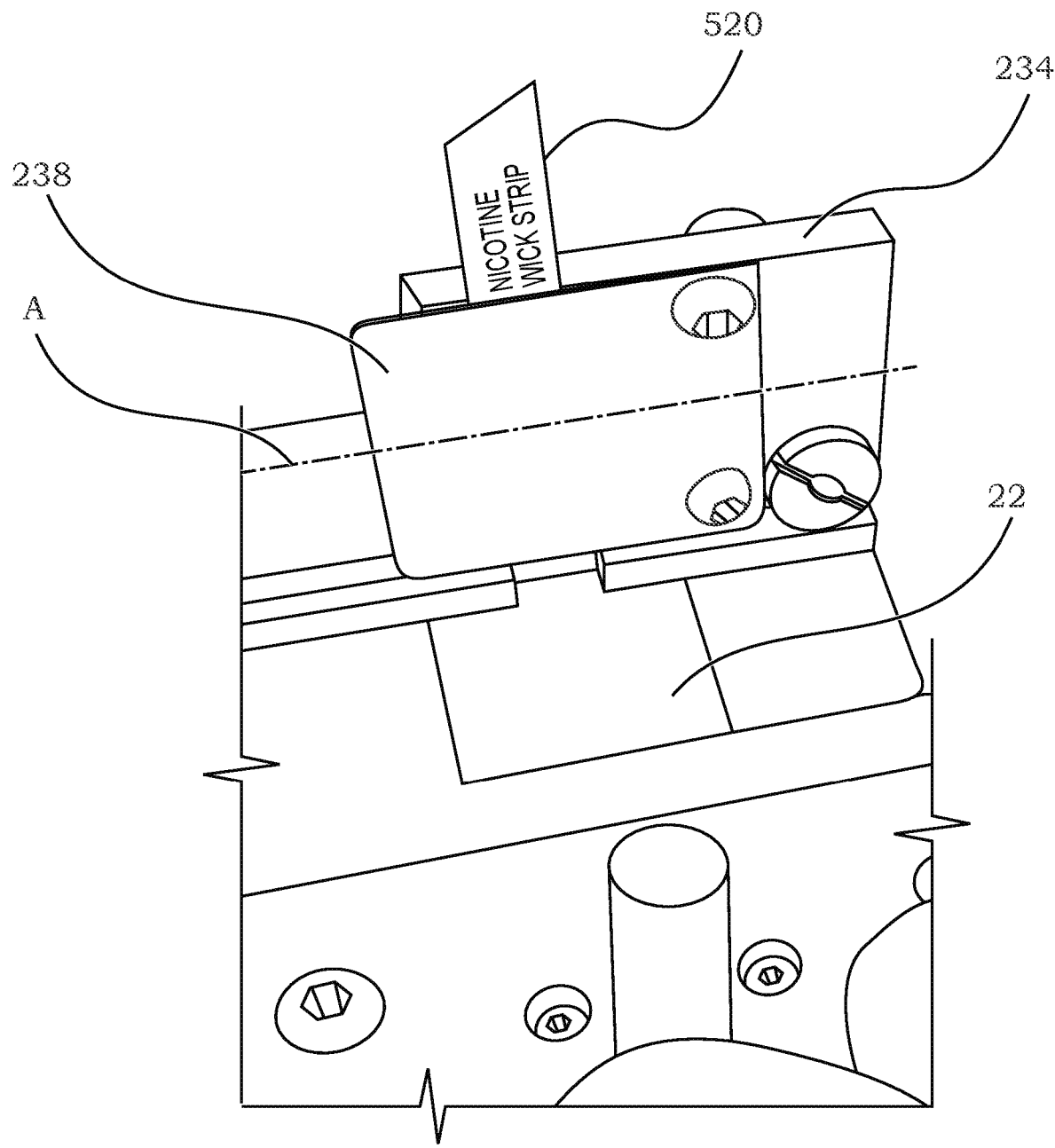
FIG. 17B illustrates an example embodiment of a method of sliding the slide illustrated in FIG. 4A to contact a portion of the wick strip.
Figure 18:
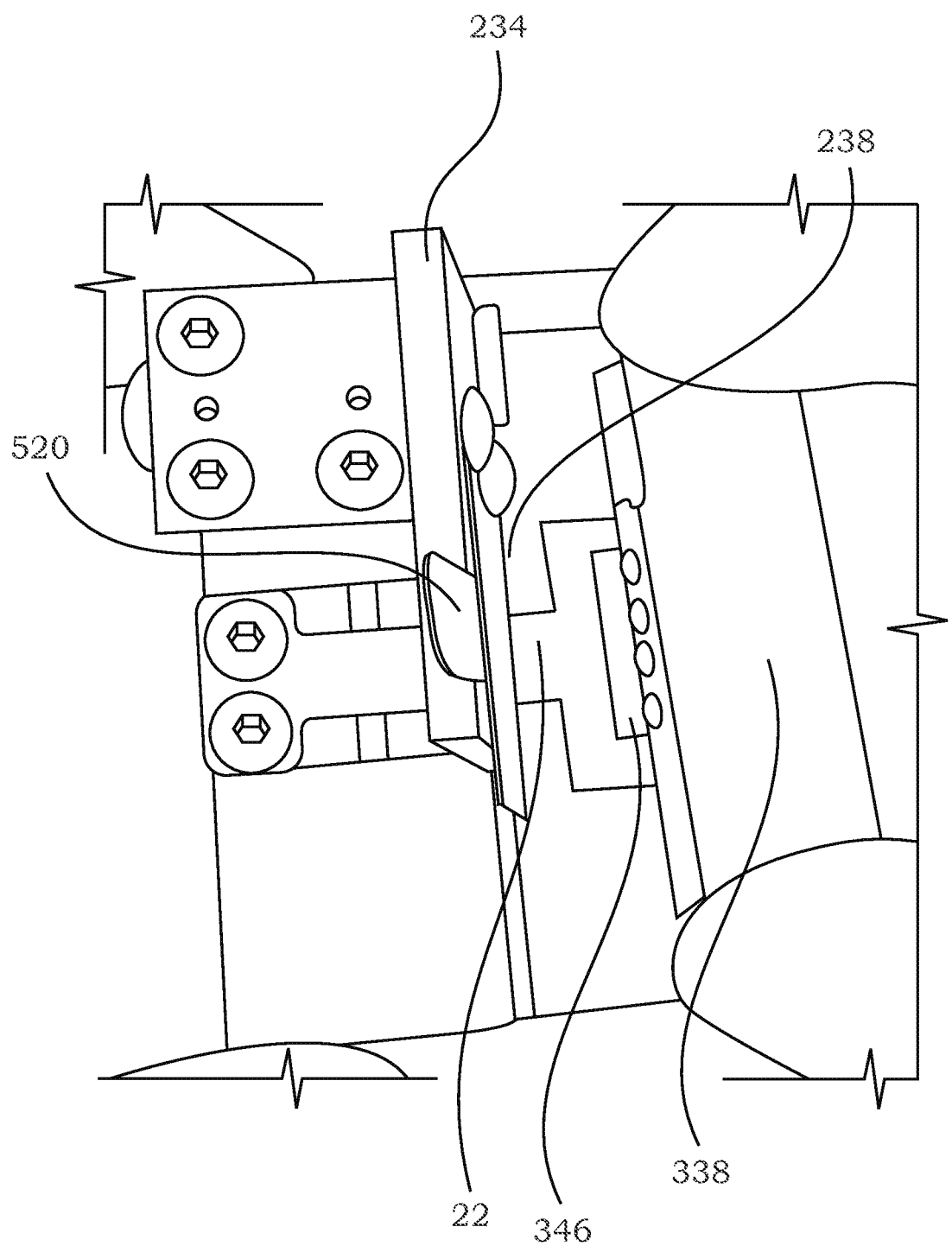
FIG. 18 illustrates an example embodiment of a method of cutting the portion of the wick strip shown in FIG. 17B from the wick strip in the channel using the cutter shown in FIG. 10.

At step 424, the end of the wick strip 520 is removed using the cutter 338. As illustrated in FIGS. 17B and 18, the slide 22 of the apparatus, or fixture, 10 is moved to a position clamping the wick strip 520 against the holder 30 to restrain movement of the wick strip 520 during cutting. The cutter 338 is moved from a position not contacting the wick strip 520 to a position contacting the wick strip 520. Specifically, the blade 346 of the cutter 338 is moved to a position slicing the wick strip 520, creating an edge that extends parallel to a plane on the top surface 154 of the slide 22.

Figure 19:
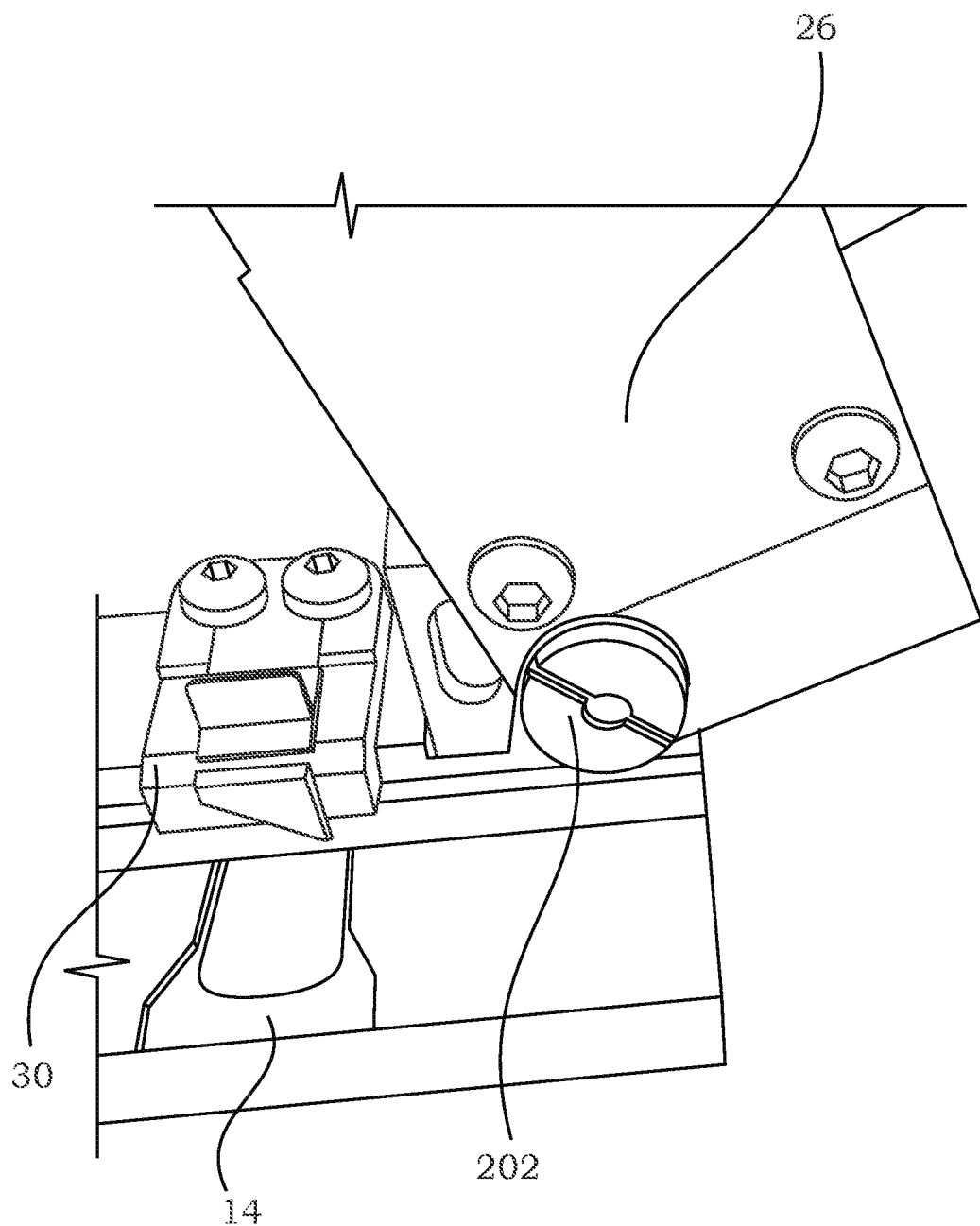
FIG. 19 illustrates an example embodiment of a method of pivoting the wick guide shown in FIGS. 9A-9B rotationally about the fastener shown in FIG. 8C.

At step 428, the wick guide 26 is rotated about the fastener 202. In at least one example embodiment, the wick guide 26 is rotatably fixed to the block 24 by a fastener 202. The body 210 of the fastener 202 extends through the wick retainer 238, the wick plate 234, and the aperture 222 in the block 24. A projection or other portion extending from a back side of the wick plate 234 may slide within the track 258 in the block 34 as the wick guide 26 rotates relative to the block 24. As illustrated in FIG. 19, the wick guide 26 may be rotated from a position where a longitudinal axis A of the wick guide 26 is parallel to a plane on the top surface 100 of the base 14 to a position where the longitudinal axis A of the wick guide 26 intersects the plane on the top surface 100 of the base 14. In some embodiments, the wick guide 26 may be rotated clockwise such that the longitudinal axis A forms an angle with the plane on the top surface 100 of the base 14 that is within a range of 45°-90°, and more specifically within a range of 75°-90°.

Figure 20A:
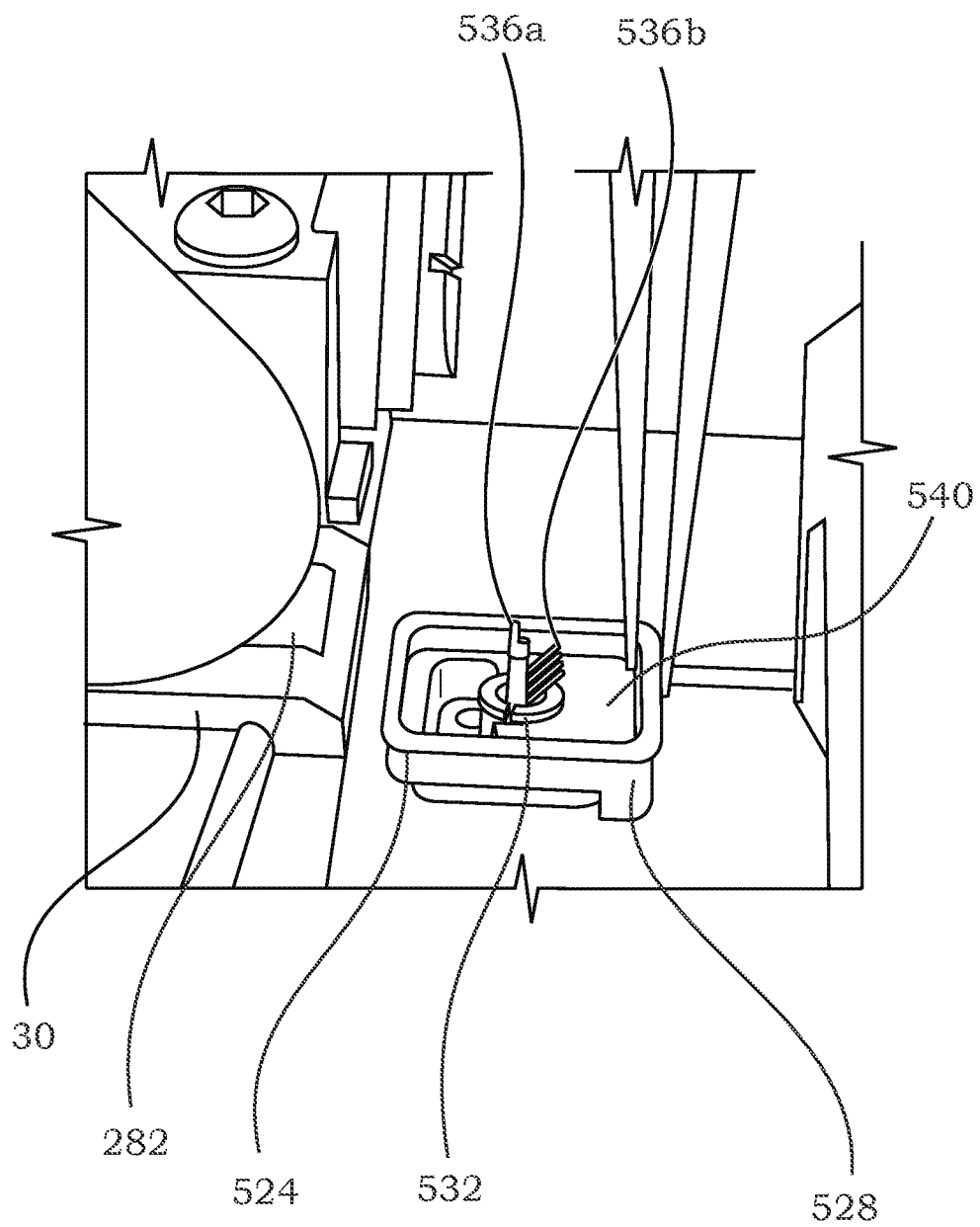
FIGS. 20A-20B illustrate an example embodiment of a method of inserting a support of a heater assembly for a nicotine pod assembly into the holder shown in FIGS. 7A-7D.

At step 432, the lever 298 on the toggle 282 of the lock 266 is engaged to move the locking fingers 286 to the first position such that the fingers are unlocked and in an open position. In some embodiments, the lock 266 may be rotatably fixed to the base 262 to rotate about a rod or pin within apertures 290 in the toggle 282. The locking fingers 286 may rotate with the rotation of the toggle 282. In one embodiment, as illustrated in FIG. 20A, lever 298 on the toggle 282 is pressed forward to move the locking fingers 286 to the first position.

The tab 322 on the opposite side of the toggle 282 from the front face 302 contacts the resilient member 270. The resilient member 270 is a flat, plate-like, spring having a body 326 and a tab or projection 330 extending from the body 326. The body 326 of the resilient member 270 is fixed to the base 262. The tab 330 extends similar to a cantilever beam and overlays the tab 322 of the toggle 282. The tab 330 of the resilient member 270 provides a counter force on the toggle 282 to bias the toggle 282 in the second, rearward, position such that the locking fingers 286 are biased in the locked, closed, position.

Thus, when the lever 298 on the toggle 282 of the lock 266 is engaged to move the locking fingers 286 to the first position, a force is exerted on the resilient member 270 by the tab 322.

Figure 20B:
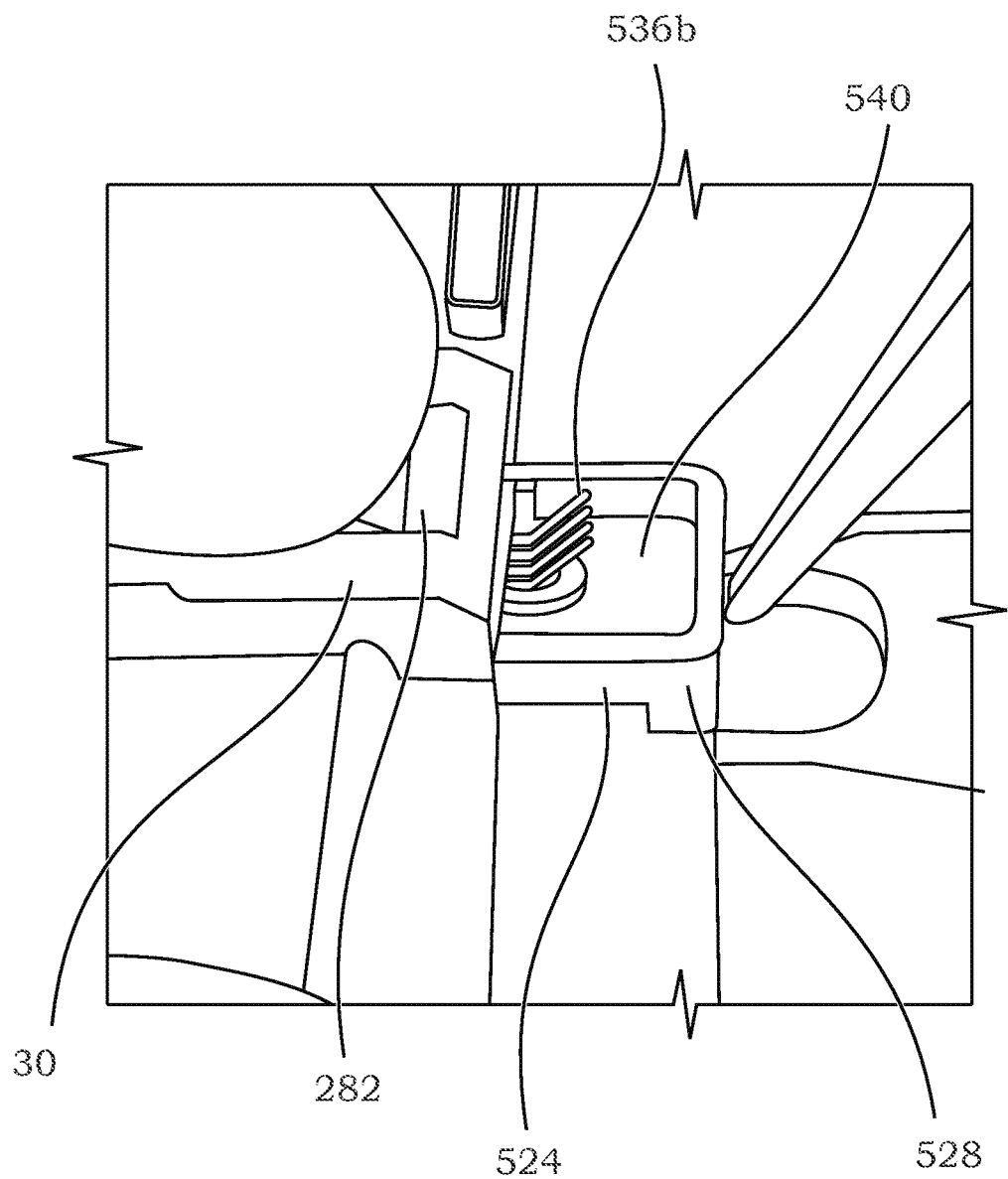

At step 436, a preliminary heater arrangement 524 (or preliminary nicotine heater arrangement) for a nicotine pod assembly is inserted into the holder 30. As illustrated in FIGS. 20A and 20B, in at least one example embodiment, the preliminary heater arrangement 524 for the nicotine pod assembly may include a base 528 and a heating element 532 having wire loops or a wire extending in a serpentine shape forming a coil 536. The wire used to form the coil may be metal. A first set of wire loops 536a may extend perpendicularly to a top surface 540 of the base 528. A second set of wire loops 536b may extend at an angle to the first set of wire loops 536a and the top surface 540. For example only, the second set of wire loops 536b may extend at an angle within a range of 30°-60° relative to the top surface 540, and more particularly, may extend at an angle of 45° relative to the top surface 540.

The heating element 532 may extend fully or partially across a width of the base 528. In some example embodiments, the heating element 532 may be in contact (for example, direct contact) with an assembled wick (further described below).

The holder 30 is disposed in the holder cutout 106 of the base 14 such that the notch 88 exists between the holder 30 and the base 14 at a location above the support cutout 110. Thus, as the preliminary heater arrangement 524 for the nicotine pod assembly is inserted into the holder 30, the base 528 is inserted into the support cutout 110 and notch 88, in a position at least partially under the holder 30.

The preliminary heater arrangement 524 for the nicotine pod assembly is inserted into the holder 30 until the first set of wire loops 536a contact the holder 30 at a location near the slots 274 on the holder 30.

At step 440, the lever 298 of the toggle 282 is released such that the toggle 282 returns to the second position. As previously stated, the tab 330 of the resilient member 270 provides a counter force on the toggle 282 to bias the toggle 282 in the second, rearward, position such that the locking fingers 286 are biased in the locked, closed, position. As shown in FIG. 20B, as the toggle 282 moves to the second position, the locking fingers 286 engage with the first set of wire loops 536a to retain the preliminary heater arrangement 524 against the holder 30.

At step 444 the wick guide 26 is rotated counterclockwise to a position where the longitudinal axis A of the wick guide 26 is parallel to a plane on the top surface 100 of the base 14. As previously stated, the wick guide 26 is rotatably fixed to the block 24 by a fastener 202. The body 210 of the fastener 202 extends through the wick retainer 238, the wick plate 234, and the aperture 222 in the block 24. The projection or other portion extending from the back side of the wick plate 234 may slide within the track 258 in the block 34 as the wick guide 26 rotates relative to the block 24. The wick guide 26 may be rotated from the position where the longitudinal axis A of the wick guide 26 intersects the plane on the top surface 100 of the base 14 to the position where the longitudinal axis A of the wick guide 26 is parallel to the plane on the top surface 100 of the base 14.

Figure 21A:
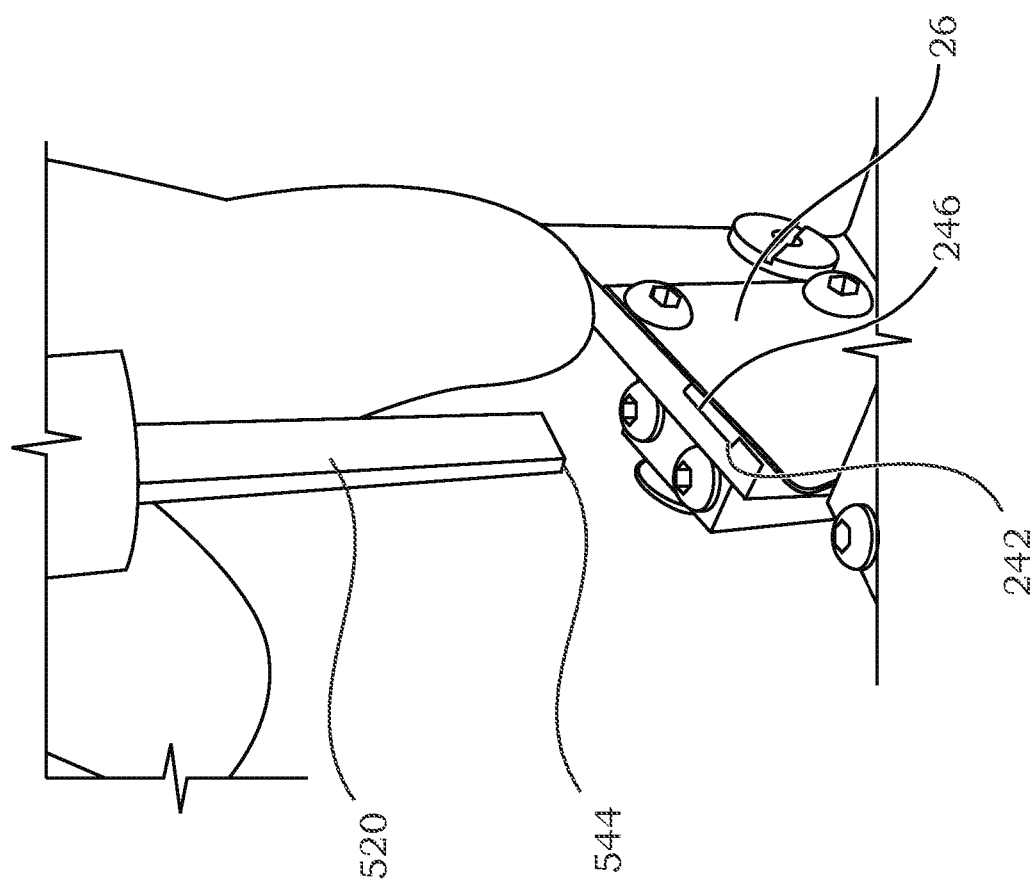
FIGS. 21A-21B illustrate an example embodiment of a method of inserting a wick into the heater assembly for the nicotine pod assembly.
Figure 21B:
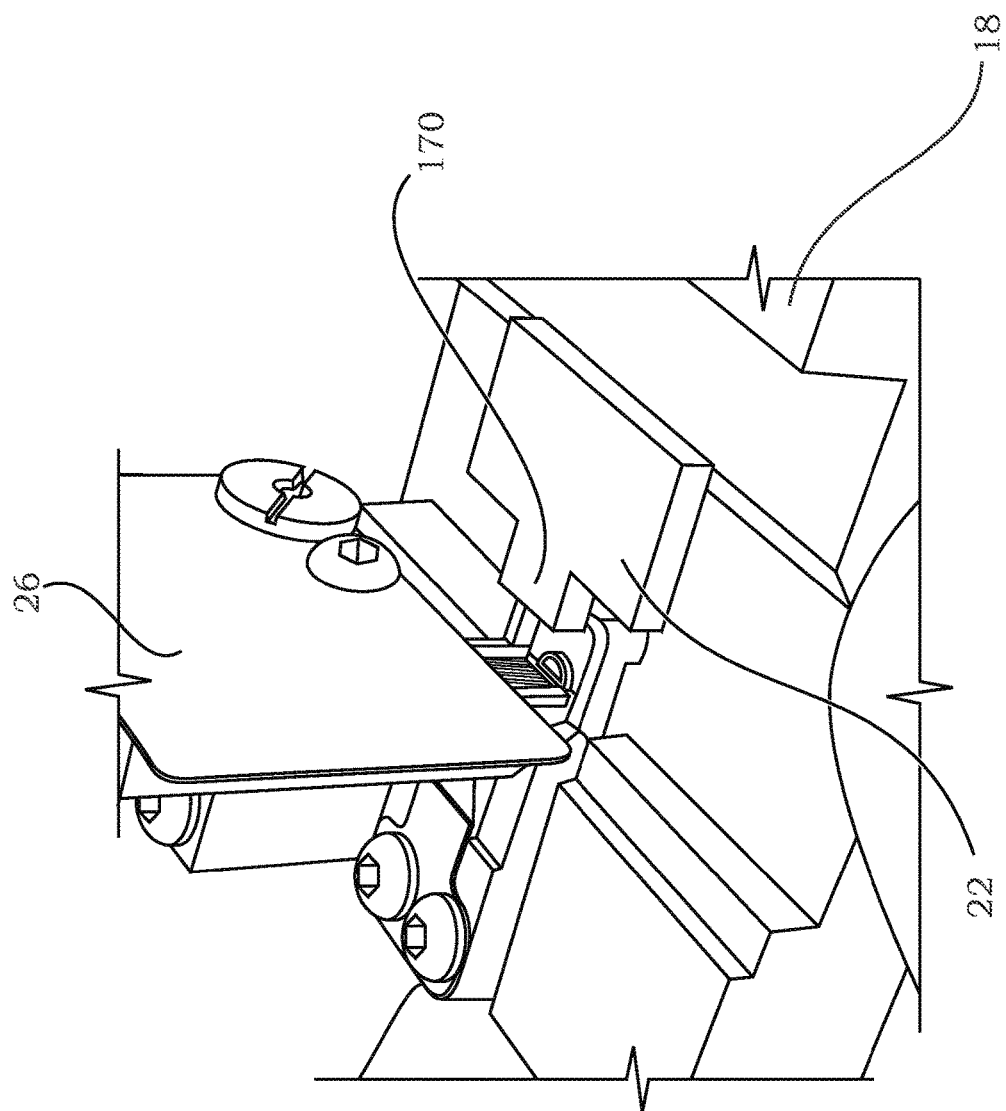

At step 448, the wick strip 520 is slid into the channel 242 in the wick guide 26 to a position contacting the top surface 540 of the base 528 of the preliminary heater arrangement 524 for the nicotine pod assembly. As illustrated in FIGS. 21A and 21B, the wick strip 520 includes an edge 544 that extends parallel to a plane on the top surface 154 of the slide 22. The edge 544 is moved into a position contacting the top surface 540 of the base 528 of the preliminary heater arrangement 524. The wick strip 520 additionally contacts the first set of wire loops 536a.

At step 452, the pin 150 of the slide 22 is moved to the fully-forward position, where the pin 150 contacts the front end 138 of the slot 126 and the plane along the front face 174 of the tab 170 on the slide 22 aligns with the plane along the sidewall 70 of the lateral channel 66.

Figure 21C:
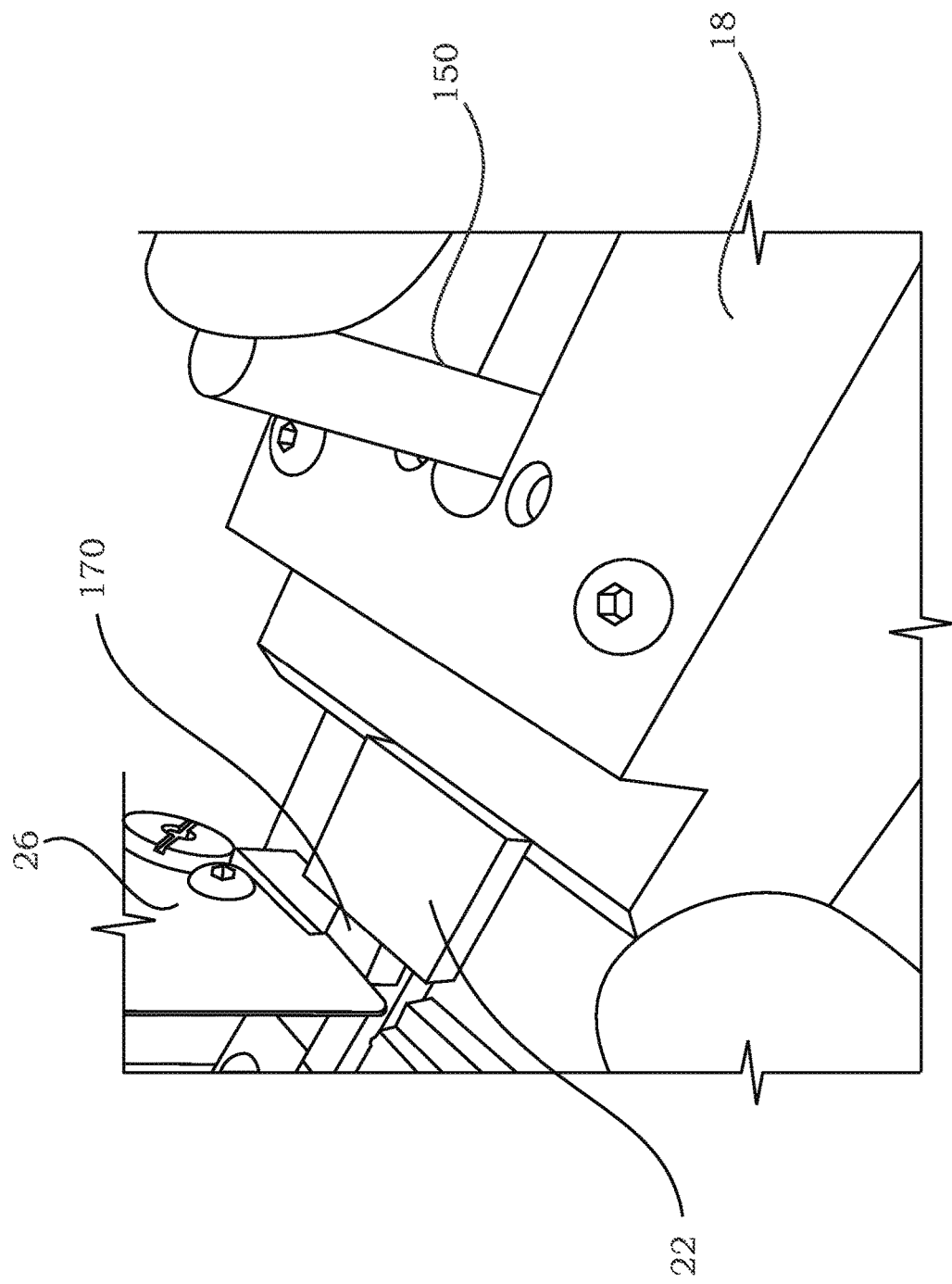
FIG. 21C illustrates an example embodiment of a method of compressing a portion of the wick between fingers of the heater assembly for the nicotine pod assembly.

As illustrated in FIGS. 21B and 21C, during movement of the slide 22 to the fully-forward position, the front face 174 of the tab 170 on the slide 22 contacts the second set of wire loops 536b and bends the second set of wire loops 536b from the position angled to the first set of wire loops 536a and the top surface 540 to a position substantially parallel to the first set of wire loops 536a and contacting the wick strip 520. In the fully-forward position, the front face 174 of the tab 170 on the slide 22 clamps the first set of wire loops 536a and the second set of wire loops 536b together to compress the wick strip 520 and fix the wick strip 520 in relation to the preliminary heater arrangement 524, forming a heater assembly, or heater-wick assembly, 524'.

Figure 21D:
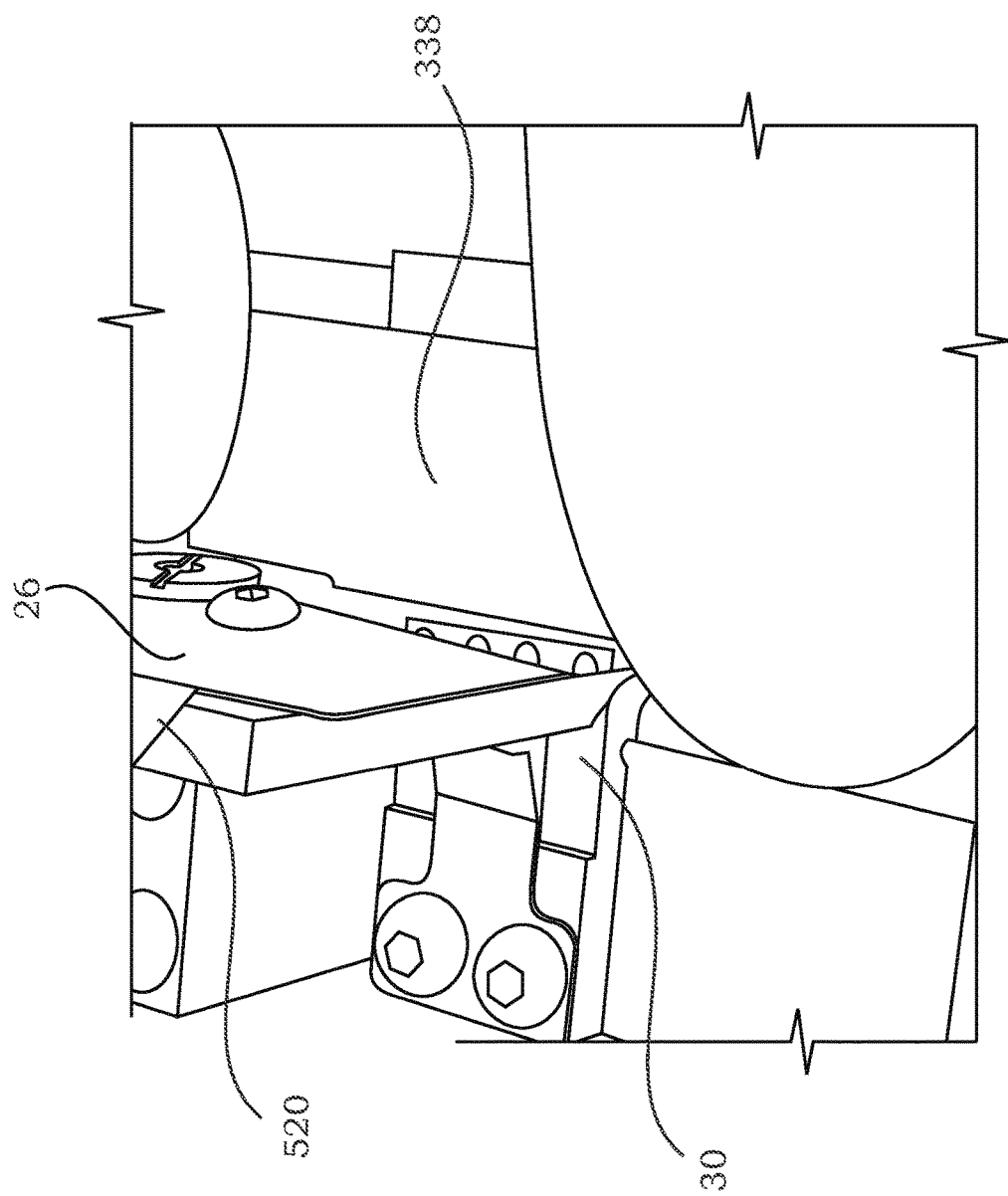
FIG. 21D illustrates an example embodiment of a method of cutting a portion of the wick.

At step 456, the wick strip 520 is cut to create a wick 548 (or nicotine wick). In some embodiments, the end of the wick strip 520 is removed using the cutter 338. As illustrated in FIG. 21D, the cutter 338 is moved from a position not contacting the wick strip 520 to a position contacting the wick strip 520. Specifically, the blade 346 of the cutter 338 is moved to a position slicing the wick strip 520, creating an edge that extends parallel to a plane on the top surface 154 of the slide 22. The resulting cut piece is the wick 548.

Figure 22:
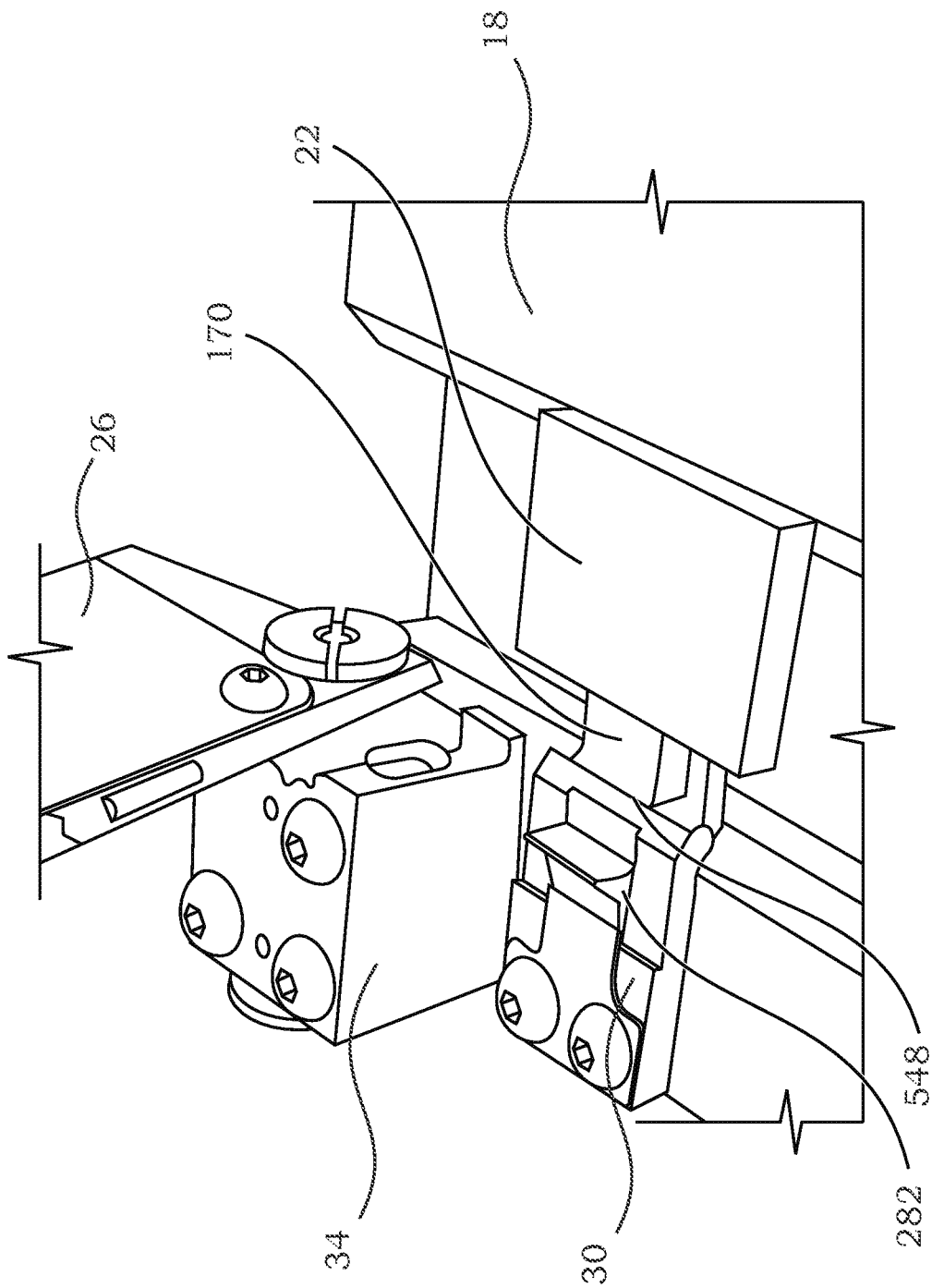
FIGS. 22-24 illustrate an example embodiment of a method of releasing the heater assembly for the nicotine pod assembly from the apparatus shown in FIG. 1A.

At step 460, the wick guide 26 is rotated clockwise. As illustrated in FIG. 22, the wick guide 26 is rotated about the fastener 202. The wick guide 26 may be rotated from a position where the longitudinal axis A of the wick guide 26 is parallel to the plane on the top surface 100 of the base 14 to a position where the longitudinal axis A of the wick guide 26 intersects the plane on the top surface 100 of the base 14. In some embodiments, the wick guide 26 may be rotated clockwise such that the longitudinal axis A forms an angle with the plane on the top surface 100 of the base 14 that is within a range of 45°-90°, and more specifically within a range of 75°-90°.

Figure 23:
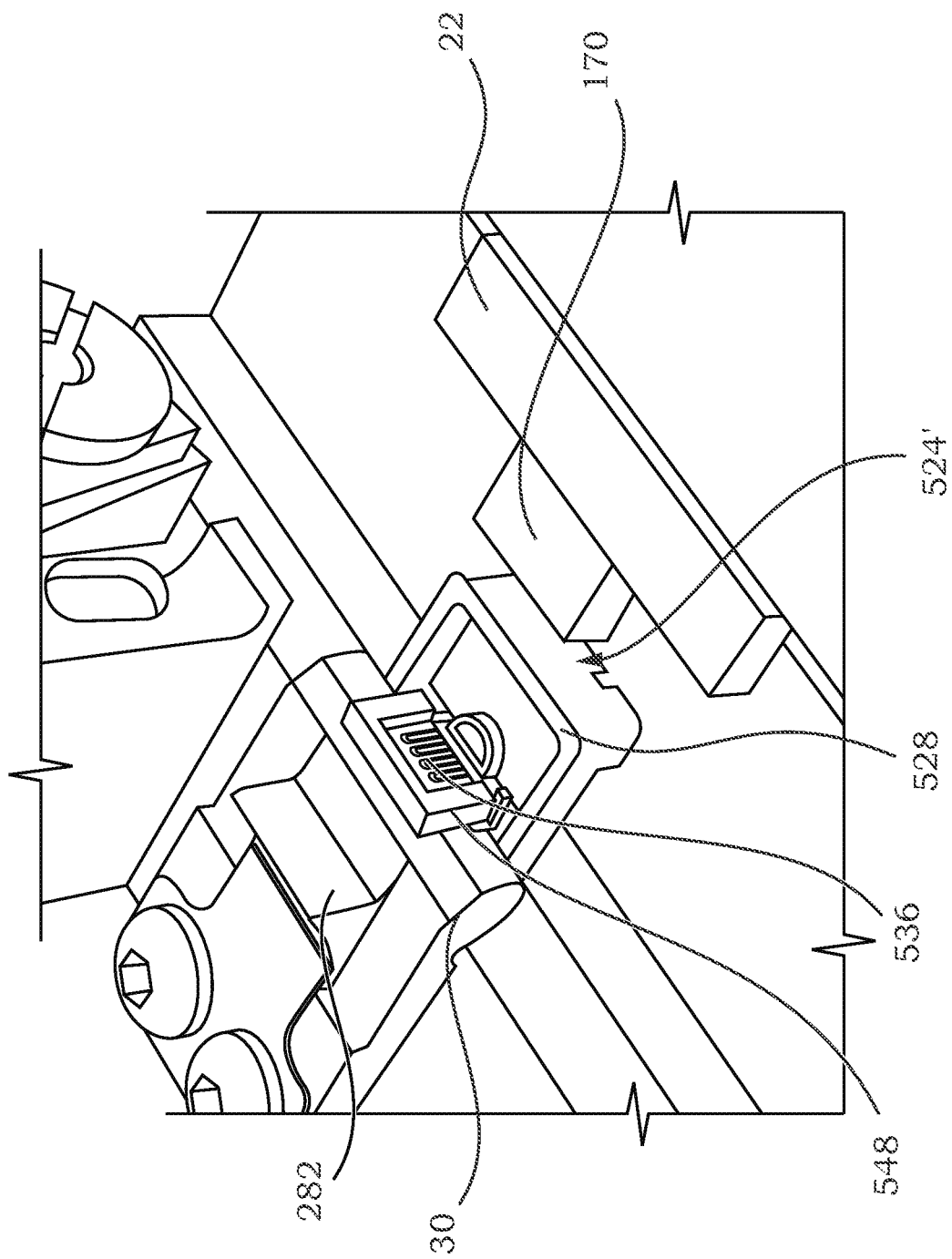

At step 464, the pin 150 of the slide 22 is moved to release the heater assembly 524' (or nicotine heater assembly) for the nicotine pod assembly. In some embodiments, the pin 150 moves to the fully-rearward position as shown in FIG. 23. In the fully-rearward position, the pin 150 may contact a rear end 178 of the slot 126 and a plane along a rear face 182 of the plate 146 of the slide 22 may align with a plane along a rear face 186 of the base 14.

Figure 24:
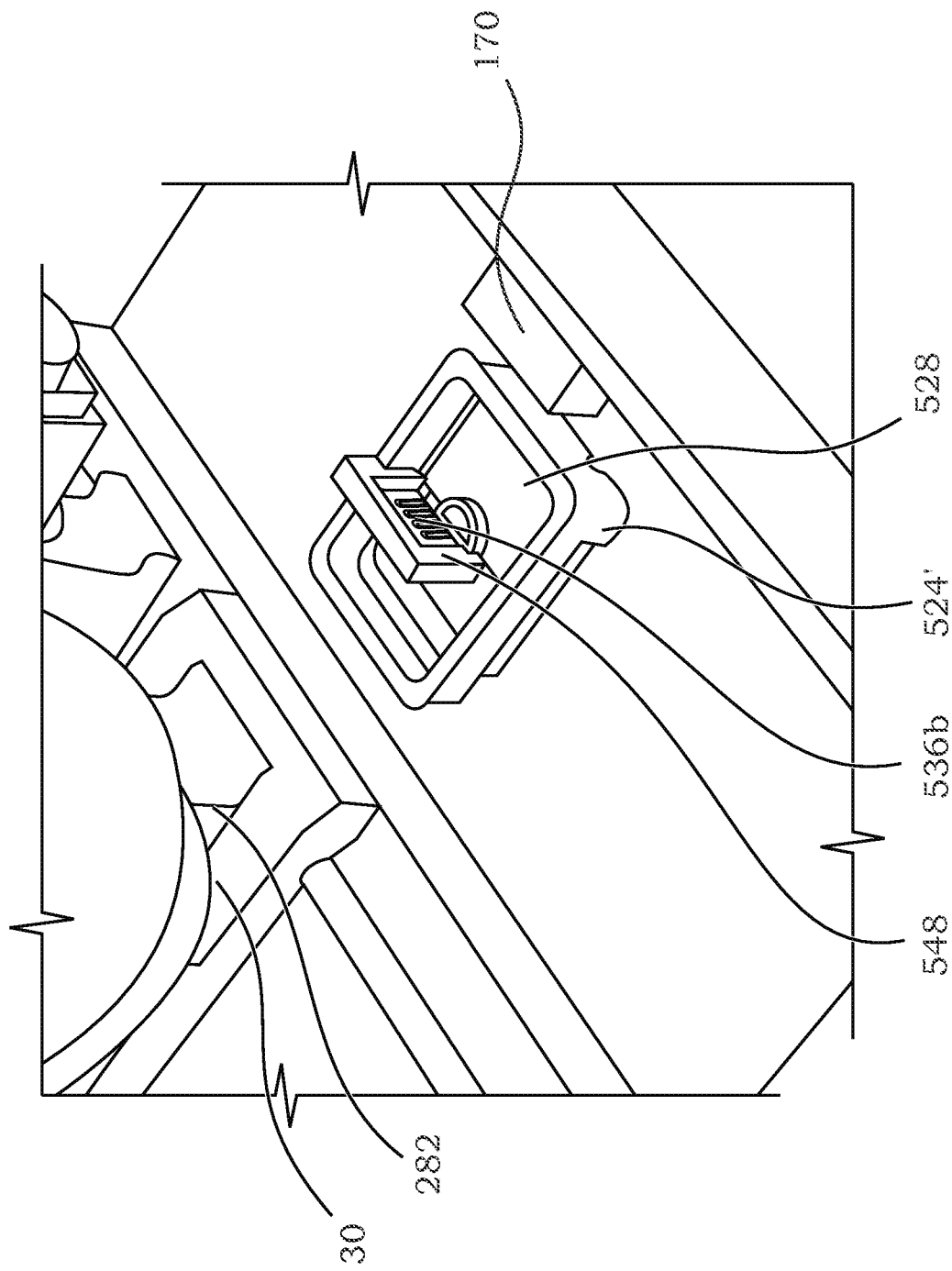

At step 468, the lever 298 of the toggle 282 is engaged to release the lock 266. Engagement of the lever 298 may move the locking fingers 286 to the first position such that the fingers are unlocked and in the open position. In some embodiments, the lock 266 may be rotatably fixed to the base 262 to rotate about a rod or pin within apertures 290 in the toggle 282. The locking fingers 286 may rotate with the rotation of the toggle 282. In one embodiment, as illustrated in FIG. 24, lever 298 on the toggle 282 is pressed forward to move the locking fingers 286 to the first position.

The tab 322 on the opposite side of the toggle 282 from the front face 302 contacts the resilient member 270. The resilient member 270 extends similar to a cantilever beam and overlays the tab 322 of the toggle 282. The resilient member 270 provides a counter force on the toggle 282 to bias the toggle 282 in the second, rearward, position such that the locking fingers 286 are biased in the locked, closed, position. Thus, when the lever 298 on the toggle 282 of the lock 266 is engaged to move the locking fingers 286 to the first position, a force is exerted on the resilient member 270 by the tab 322.

At step 472, the heater assembly 524' for the nicotine pod assembly is removed from the holder 30. As illustrated in FIGS. 23 and 24, the heater assembly 524' is removed from the holder 30 by sliding the heater assembly 524' in the notch 88 and support cutout 110 away from the holder 30 until the heater assembly 524' clears an edge of the holder 30. The heater assembly 524' for the nicotine pod assembly is then removed from the support cutout 110.

At step 476, the lever 298 of the toggle 282 is released such that the toggle 282 returns to the second position. As previously stated, the tab 330 of the resilient member 270 provides a counter force on the toggle 282 to bias the toggle 282 in the second, rearward, position such that the locking fingers 286 are biased in the locked, closed, position.

At step 480, method 400 ends.

Figure 25:
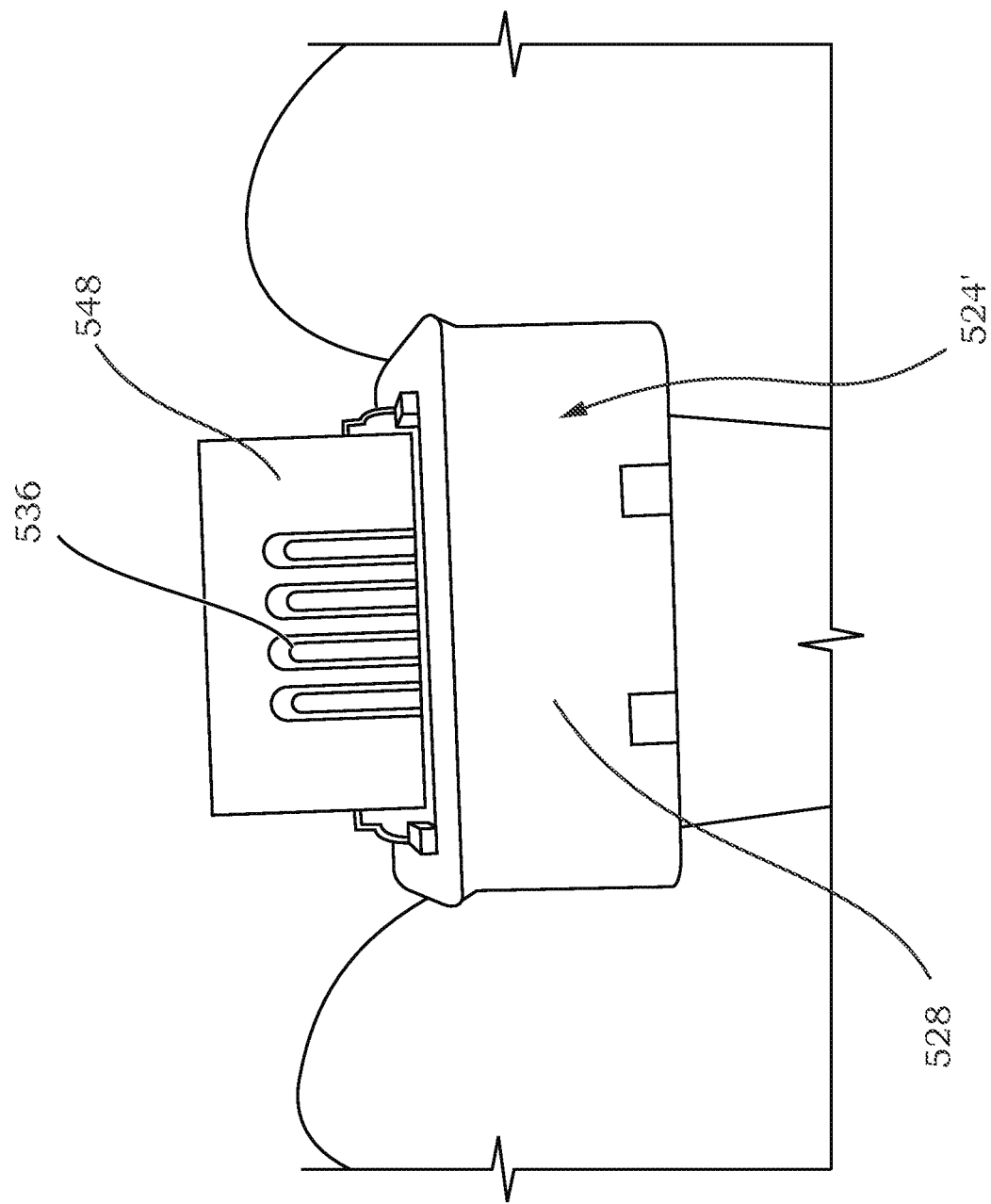
FIG. 25 is a front view of an example embodiment of an assembled heater assembly for a nicotine pod assembly.

Now referring to FIG. 25, an embodiment of an assembled heater assembly 524' for a nicotine pod assembly is illustrated. The wick 548 is clamped between the first set of wire loops 536a and the second set of wire loops 536b such that the wick 548 is fixed relative to the heater assembly 524'. An example heater assembly is disclosed in U.S. application Ser. No. 16/696,007, filed Nov. 26, 2019, titled "NICOTINE POD ASSEMBLIES AND NICOTINE E-VAPING DEVICES," the disclosure of which is incorporated herein in its entirety by reference.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, or the like, may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments have been disclosed herein. It should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An apparatus for assembling a heater assembly for a nicotine pod assembly, the apparatus comprising:
 a base;
 a wick feed extending toward the base and defining a channel configured to receive a wick structured to draw a nicotine pre-vapor formulation via capillary action;
 a slide configured to move along a plane on a top face of the base; and
 a holder disposed on the top face of the base,
 wherein the holder is configured to secure a support of the heater assembly, the slide includes a front face that is orthogonal to the top face of the base, and the slide is configured to contact a finger of a heater on the support to move the finger to a vertical position so as to compress the wick.

2. The apparatus of claim 1, further comprising:
 a wick retainer extending parallel and adjacent to the wick feed for retaining the wick in the channel.

3. The apparatus of claim 1, further comprising:
 a cutter having a blade configured to slide along a top surface of the slide to cut the wick.

4. The apparatus of claim 1, wherein the wick feed is configured to rotate relative to the base.

5. The apparatus of claim 1, further comprising:
 a block fixed to the base,
 wherein the wick feed is rotatably attached to and supported by the block.

6. The apparatus of claim 1, wherein the holder is configured to receive the support of the heater assembly therein, the holder being configured to fix the support relative to the base for inserting the wick.

7. The apparatus of claim 6, wherein the channel in the wick feed is configured to guide the wick into alignment with the heater on the support.

8. The apparatus of claim 1, wherein the wick feed extends orthogonally to the base.

9. The apparatus of claim 1, wherein the holder includes a locking finger configured to engage the support of the heater assembly and retain the support within the holder.

10. The apparatus of claim 1, wherein the wick feed includes a plate and a retainer, the plate is disposed orthogonal to the base and defines the channel, and the retainer is disposed orthogonal to the base and adjacent to the plate, the retainer and the plate defining a slot for guiding the wick.

11. The apparatus of claim 10, further comprising:
a block fixed to the base,
wherein the plate is rotatably attached to and supported by the block.

12. The apparatus of claim 11, wherein the retainer is fixed to the plate such that the retainer and the plate are configured to rotate relative to the base and the block.

13. The apparatus of claim 1, wherein the holder is configured to secure the support of the heater assembly and to lock a position of the support relative to the base.

14. The apparatus of claim 13, wherein the holder includes a locking finger configured to engage the support and retain the support within the holder.

15. The apparatus of claim 1, further comprising:
a blade configured to slide along a top surface of the slide.

16. A method of assembling a heater assembly for a nicotine pod assembly, the method comprising:
securing, with a holder, a support of the heater assembly relative to a base;
aligning, with a wick feed mounted to the base, a wick in a heater of the support, the wick structured to draw a nicotine pre-vapor formulation via capillary action;
cutting, with a blade configured to slide relative to the base, a portion of the wick;
clamping, with a slide configured to move along a plane on a top face of the base, a portion of the heater around the portion of the wick; and
releasing, with the holder, the support from the base,
wherein the holder is disposed on the top face of the base,
wherein the wick feed extends toward the base and defines a channel configured to receive the wick,
wherein the slide includes a front face that is orthogonal to the top face of the base, and the slide is configured to contact a finger of the heater on the support to move the finger to a vertical position so as to compress the wick.

17. The method of claim 16, wherein the securing the support relative to the base includes locking the support in the holder.

18. The method of claim 16, wherein the aligning the wick in the heater of the support includes inserting the wick into the channel in the wick feed plate.

19. The method of claim 16, wherein the aligning the wick in the heater of the support includes inserting the wick into a gap defined by the channel in the wick feed and a retainer plate fixed to the wick feed.

* * * * *